(12) United States Patent
Francis et al.

(10) Patent No.: US 11,219,711 B2
(45) Date of Patent: *Jan. 11, 2022

(54) SYSTEM AND METHOD FOR HYBRID CONTROL OF REDUCED PRESSURES DELIVERED TO A TISSUE SITE

(71) Applicant: KCI Licensing, Inc., San Antonio, TX (US)

(72) Inventors: Loren Francis, San Antonio, TX (US); Reuben W. Edgar, Jr., San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 489 days.

This patent is subject to a terminal disclaimer.

(21) Appl. No.: 16/158,525

(22) Filed: Oct. 12, 2018

(65) Prior Publication Data
US 2019/0125942 A1 May 2, 2019

Related U.S. Application Data

(63) Continuation of application No. 14/995,871, filed on Jan. 14, 2016, now Pat. No. 10,124,093.
(Continued)

(51) Int. Cl.
*A61M 35/00* (2006.01)
*A61M 1/00* (2006.01)
(Continued)

(52) U.S. Cl.
CPC ............... *A61M 1/73* (2021.05); *A61M 1/74* (2021.05); *A61M 1/90* (2021.05);
(Continued)

(58) Field of Classification Search
CPC ........ A61M 35/00; A61M 1/00; A61M 27/00; A61M 22/15; A61M 22/33;
(Continued)

(56) References Cited

U.S. PATENT DOCUMENTS 1,355,846 A 10/1920 Rannells
2,547,758 A 4/1951 Keeling
(Continued)

FOREIGN PATENT DOCUMENTS

AU 550575 B2 3/1986
AU 745271 B2 3/2002
(Continued)

OTHER PUBLICATIONS

Louis C. Argenta, MD and Michael J. Morykwas, PHD; Vacuum-Assisted Closure: A New Method for Wound Control and Treatment: Clinical Experience; Annals of Plastic Surgery; vol. 38, No. 6, Jun. 1997; pp. 563-576.
(Continued)

*Primary Examiner* — Tatyana Zalukaeva
*Assistant Examiner* — Ilya Y Treyger

(57) ABSTRACT

In one example embodiment, a system for stimulating healing of tissue at a wound site is disclosed. The system comprises a dressing including a porous pad and a drape covering the pad at a wound site for maintaining negative pressure at a wound site, a negative-pressure source including a pump and an electric motor to generate a pump pressure (PP) for applying to the wound site, and a first pressure sensor for sensing the pump pressure (PP). The system further comprises a controller coupled to the first pressure sensor and electric motor and including a PID controller that compares the pump pressure (PP) to a target pump pressure (TPP) and a bang-bang controller that controls wound pressure (WP) proximate the wound site, and wherein the controller is configured to alternatively select the bang-bang controller when the system is in a low-leakage condition or the PID controller when the system is in a high-leakage condition.

31 Claims, 8 Drawing Sheets

Related U.S. Application Data

(60) Provisional application No. 62/104,529, filed on Jan. 16, 2015.

(51) Int. Cl.

A61M 27/00 (2006.01)
  A61F 13/00 (2006.01)
  A61F 13/02 (2006.01)

(52) U.S. Cl.
 CPC . *A61M 2205/15* (2013.01); *A61M 2205/3331* (2013.01); *A61M 2205/3334* (2013.01); *A61M 2205/3341* (2013.01); *A61M 2205/3344* (2013.01); *A61M 2205/50* (2013.01)

(58) Field of Classification Search
 CPC .. A61M 2205/3331; A61M 2205/3334; A61M 2205/3341; A61M 2205/3344; A61M 2205/50; A67F 13/00; A67F 13/02; A61F 13/00; A61F 13/02
 See application file for complete search history.

(56) References Cited

U.S. PATENT DOCUMENTS

| | | |
|---|---|---|
| 2,632,443 A | 3/1953 | Lesher |
| 2,682,873 A | 7/1954 | Evans et al. |
| 2,910,763 A | 11/1959 | Lauterbach |
| 2,969,057 A | 1/1961 | Simmons |
| 3,066,672 A | 12/1962 | Crosby, Jr. et al. |
| 3,367,332 A | 2/1968 | Groves |
| 3,520,300 A | 7/1970 | Flower, Jr. |
| 3,568,675 A | 3/1971 | Harvey |
| 3,648,692 A | 3/1972 | Wheeler |
| 3,682,180 A | 8/1972 | McFarlane |
| 3,826,254 A | 7/1974 | Mellor |
| 4,080,970 A | 3/1978 | Miller |
| 4,096,853 A | 6/1978 | Weigand |
| 4,139,004 A | 2/1979 | Gonzalez, Jr. |
| 4,165,748 A | 8/1979 | Johnson |
| 4,184,510 A | 1/1980 | Murry et al. |
| 4,233,969 A | 11/1980 | Lock et al. |
| 4,245,630 A | 1/1981 | Lloyd et al. |
| 4,256,109 A | 3/1981 | Nichols |
| 4,261,363 A | 4/1981 | Russo |
| 4,275,721 A | 6/1981 | Olson |
| 4,284,079 A | 8/1981 | Adair |
| 4,297,995 A | 11/1981 | Golub |
| 4,333,468 A | 6/1982 | Geist |
| 4,373,519 A | 2/1983 | Errede et al. |
| 4,382,441 A | 5/1983 | Svedman |
| 4,392,853 A | 7/1983 | Muto |
| 4,392,858 A | 7/1983 | George et al. |
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 7,022,113 B2 | 4/2006 | Lockwood et al. |
| 7,625,362 B2 | 12/2009 | Boehringer et al. |
| 7,846,141 B2 | 12/2010 | Weston |
| 8,062,273 B2 | 11/2011 | Weston |
| 8,216,198 B2 | 7/2012 | Heagle et al. |
| 8,251,979 B2 | 8/2012 | Malhi |
| 8,257,327 B2 | 9/2012 | Blott et al. |
| 8,323,264 B2 | 12/2012 | Weston et al. |
| 8,398,614 B2 | 3/2013 | Blott et al. |
| 8,444,613 B2 | 5/2013 | Svedman et al. |
| 8,449,509 B2 | 5/2013 | Weston |
| 8,529,548 B2 | 9/2013 | Blott et al. |
| 8,535,296 B2 | 9/2013 | Blott et al. |
| 8,551,060 B2 | 10/2013 | Schuessler et al. |
| 8,568,386 B2 | 10/2013 | Malhi |
| 8,663,200 B2 | 3/2014 | Weston et al. |
| 8,679,081 B2 | 3/2014 | Heagle et al. |
| 8,834,451 B2 | 9/2014 | Blott et al. |
| 8,926,592 B2 | 1/2015 | Blott et al. |
| 9,017,302 B2 | 4/2015 | Vitaris et al. |
| 9,198,801 B2 | 12/2015 | Weston |
| 9,211,365 B2 | 12/2015 | Weston |
| 9,289,542 B2 | 3/2016 | Blott et al. |
| 9,308,714 B2 | 4/2016 | Bedell et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2014/0163491 A1 | 6/2014 | Schuessler et al. |
| 2015/0080788 A1 | 3/2015 | Blott et al. |

(56) References Cited

U.S. PATENT DOCUMENTS

FOREIGN PATENT DOCUMENTS

| | | |
|---|---|---|
| AU | 755496 B2 | 12/2002 |
| CA | 2005436 A1 | 6/1990 |
| DE | 26 40 413 A1 | 3/1978 |
| DE | 43 06 478 A1 | 9/1994 |
| DE | 29 504 378 U1 | 9/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 A1 | 7/2000 |
| GB | 692578 A | 6/1953 |
| GB | 2 195 255 A | 4/1988 |
| GB | 2 197 789 A | 6/1988 |
| GB | 2 220 357 A | 1/1990 |
| GB | 2 235 877 A | 3/1991 |
| GB | 2 329 127 A | 3/1999 |
| GB | 2 333 965 A | 8/1999 |
| JP | 4129536 B2 | 8/2008 |
| SG | 71559 | 4/2002 |
| WO | 80/02182 A1 | 10/1980 |
| WO | 87/04626 A1 | 8/1987 |
| WO | 90/010424 A1 | 9/1990 |
| WO | 93/009727 A1 | 5/1993 |
| WO | 94/020041 A1 | 9/1994 |
| WO | 96/05873 A1 | 2/1996 |
| WO | 97/18007 A1 | 5/1997 |
| WO | 99/13793 A1 | 3/1999 |

OTHER PUBLICATIONS

Susan Mendez-Eatmen, RN; "When wounds Won't Heal" RN Jan. 1998, vol. 61 (1); Medical Economics Company, Inc., Montvale, NJ, USA; pp. 20-24.
James H. Blackburn II, MD et al.: Negative-Pressure Dressings as a Bolster for Skin Grafts; Annals of Plastic Surgery, vol. 40, No. 5, May 1998, pp. 453-457; Lippincott Williams & Wilkins, Inc., Pnilidelphia, PA, USA.
John Masters; "Reliable, Inexpensive and Simple Suction Dressings"; Letter to the Editor, British Journal of Plastic Surgery, 1998, vol. 51 (3), p. 267; Elsevier Science/The British Association of Plastic Surgeons, UK.
S.E. Greer, et al. "The Use of Subatmospheric Pressure Dressing Therapy to Close Lymphocutaneous Fistulas of the Groin" British Journal of Plastic Surgery (2000), 53, pp. 484-487.
George V. Letsou, MD., et al.; "Stimulation of Adenylate Cyclase Activity in Cultured Endothelial Cells Subjected to Cyclic Stretch"; Journal of Cardiovascular Surgery, 31, 1990, pp. 634-639.
Orringer, Jay, et al.; "Management of Wounds in Patients with Complex Enterocutaneous Fistulas"; Surgery, Gynecology & Obstetrics, Jul. 1987, vol. 165, pp. 79-80.
International Search Report for PCT International Application PCT/GB95/01983; dated Nov. 23, 1995.
PCT international Search Report for PCT International Application PCT/GB98/02713; dated Jan. 8, 1999.
PCT Written Opinion; PCT International Application PCT/GB98/02713; dated Jun. 8, 1999.
PCT International Examination and Search Report, PCT International Application PCT/GE96/02802; dated Jan. 15, 1998 & dated Apr. 29, 1997.
PCT Written Opinion, PCT International Application PCT/GB96/02802; dated Sep. 3, 1997.
Dattilo, Philip P., Jr., et al.; "Medical Textiles: Application of an Absorbable Barbed Bi-directional Surgical Suture"; Journal of Textile and Apparel, Technology and Management, vol. 2, Issue 2, Spring 2002, pp. 1-5.
Kostyuchenok, B.M., et al.; "Vacuum Treatment in the Surgical Management of Purulent Wounds"; Vestnik Khirurgi, Sep. 1986, pp. 18-21 and 6 page English translation thereof.
Davydov, Yu, A., et al.; "Vacuum Therapy in the Treatment of Purulent Lactation Mastitis"; Vestnik Khirurgi, May 14, 1986, pp. 66-70, and 9 page English translation thereof.
Yusupov. Yu.N., et al.; "Active Wound Drainage", Vestnki Khirurgi, vol. 138, Issue 4, 1987, and 7 page English translation thereof.
Davydov, Yu.A., et al.; "Bacteriological and Cytological Assessment of Vacuum Therapy for Purulent Wounds" Vestnik Khirugi, Oct. 1988, pp. 48-52, and 8 page English translation thereof.
Davydov, Yu.A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.
Chariker, Mark E., M.D., et al; "Effective Management of incisional and cutaneous fistulae with closed suction wound drainage"; Contemporary Surgery, vol. 34, Jun. 1989, pp. 59-63.
Egnell Minor, Instruction Book, First Edition, 300 7502, Feb. 1975, pp. 24.
Egnell Minor: Addition to the Users Manual Concerning Overflow Protection—Concerns all Egnell Pumps, Feb. 3, 1983, pp. 2.
Svedman, P.: "Irrigation Treatment of Leg Ulcers", The Lancet, Sep. 3, 1983, pp. 532-534.
Chinn, Steven D. et al.: "Closed Wound Suction Drainage", The Journal of Foot Surgery, vol. 24, No. 1, 1985, pp. 76-81.
Arnljots, Björn et al.: "irrigation Treatment in Split-Thickness Skin Grafting of intractable Leg Ulcers", Scand J. Plast Reconstr. Surg., No. 19, 1985, pp. 211-213.
Svedman, P.: "A Dressing Allowing Continuous Treatment of a Biosurface", IRCS Medical Science: Biomedical Technology, Clinical Medicine, Surgery and Transplantation, vol. 7, 1979, p. 221.
Svedman, P. et al.: "A Dressing System Providing Fluid Supply and Suction Drainage Used for Continuous of Intermittent Irrigation", Annals of Plastic Surgery, vol. 17, No. 2, Aug. 1986, pp. 125-133.
N.A. Bagautdinov, "Variant of External Vacuum Aspiration in the Treatment of Purulent Diseases of Soft Tissues," Current Problems in Modern Clinical Surgery: Interdepartmental Collection, edited by V. Ye Volkov et al. (Chuvashia State University, Cheboksary, U.S.S.R. 1986); pp. 94-96 (copy and certified translation).
K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.
G. Živadinovi?, V. ?uki?, Ž. Maksimovi?, ?. Radak, and P. Peška, "Vacuum Therapy in the Treatment of Peripheral Blood Vessels," Timok Medical Journal 11 (1986), pp. 161-164 (copy and certified translation).
F.E. Johnson, "An Improved Technique for Skin Graft Placement Using a Suction Drain," Surgery, Gynecology, and Obstetrics 159 (1984), pp. 584-585.
A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).
M. Schein, R. Saadia, J.R. Jamieson, and G.A.G. Decker, "The 'Sandwich Technique' in the Management of the Open Abdomen," British Journal of Surgery 73 (1986), pp. 369-370.
D.E. Tribble, An Improved Sump Drain-Irrigation Device of Simple Construction, Archives of Surgery 105 (1972) pp. 511-513.
M.J. Morykwas, L.C. Argenta, E.I. Shelton-Brown, and W. McGuirt, "Vacuum-Assisted Closure: A New Method for Wound Control and Treatment: Animal Studies and Basic Foundation," Annals of Plastic Surgery 38 (1997), pp. 553-562 (Morykwas I).
C.E. Tennants, "The Use of Hypermia in the Postoperative Treatment of Lesions of the Extremities and Thorax, "Journal of the American Medical Association 64 (1915), pp. 1548-1549.
Selections from W. Meyer and V. Schmieden, Bier's Hyperemic Treatment in Surgery, Medicine, and the Specialties: A Manual of Its Practical Application, (W.B. Saunders Co., Philadelphia, PA 1909), pp. 17-25, 44-64, 90-96, 167-170, and 210-211.
V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical institute, Gorky, U.S.S.R. 1987) ("Solovev Guidelines").

(56) References Cited

OTHER PUBLICATIONS

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention or Suture Fanures after Gastric Resection (S.M. Kirov Gorky State Medical Institute, Gorky, U.S.S.R, 1988) ("Solovev Abstract").

V.A.C.® Therapy Clinical Guidelines: A Reference Source for Clinicians; Jul. 2007.

SYSTEM AND METHOD FOR HYBRID CONTROL OF REDUCED PRESSURES DELIVERED TO A TISSUE SITE

The present invention is a continuation of U.S. application Ser. No. 14/995,871, entitled "SYSTEM AND METHOD FOR HYBRID CONTROL OF REDUCED PRESSURES DELIVERED TO A TISSUE SITE", filed Jan. 14, 2016, which claims the benefit under 35 U.S.C. § 119(e), of the filing of U.S. Provisional Patent Application Ser. No. 62/104,529, entitled "SYSTEM AND METHOD FOR HYBRID CONTROL OF REDUCED PRESSURES DELIVERED TO A TISSUE SITE", filed Jan. 16, 2015, all of which are incorporated by reference in their entirety.

TECHNICAL FIELD

The inventions as set forth in the appended claims relate generally to a negative-pressure tissue treatment system and method and more particularly, but without limitation, to a hybrid control of therapy pressures applied by such tissue treatment system and method to a tissue site wherein the therapy pressures may be varied based on the pressure leakage of the tissue treatment system and method.

BACKGROUND

Clinical studies and practice have shown that reducing pressure in proximity to a tissue site can augment and accelerate growth of new tissue at the tissue site. The applications of this phenomenon are numerous, but it has proven particularly advantageous for treating wounds. Regardless of the etiology of a wound, whether trauma, surgery, or another cause, proper care of the wound is important to the outcome. Treatment of wounds or other tissue with reduced pressure may be commonly referred to as "negative-pressure therapy," but is also known by other names, including "negative-pressure wound therapy," "reduced-pressure therapy," "vacuum therapy," and "vacuum-assisted closure," for example. Negative-pressure therapy may provide a number of benefits, including migration of epithelial and subcutaneous tissues, improved blood flow, and micro-deformation of tissue at a wound site. Together, these benefits can increase development of granulation tissue and reduce healing times.

While the clinical benefits of negative-pressure therapy are widely known, the cost and complexity of negative-pressure therapy can be a limiting factor in its application, and the development and operation of negative-pressure systems, components, and processes continues to present significant challenges to manufacturers, healthcare providers, and patients.

BRIEF SUMMARY

New and useful systems, apparatuses, and methods for maintaining negative pressure in low and high leak conditions in a negative-pressure therapy environment are set forth in the appended claims. Illustrative embodiments are also provided to enable a person skilled in the art to make and use the claimed subject matter.

The reduced pressure provided by a reduced pressure treatment system to a tissue site such as, for example, an incision or a wound, may need to be properly controlled to increase the effectiveness of the reduced pressure treatment. The reduced pressure treatment system may include a pump for providing reduced pressure, a wound dressing disposed adjacent the wound, and a drape that covers both to provide a sealed environment for providing the reduced pressure treatment from the pump to the sealed environment. Leaks and blockages may occur in the components of the reduced pressure treatment system such as, for example, leaks between the drape and the tissue site, that may need to be detected in order to adjust the pressure provided by the pump to maintain effective treatment.

The type of method used for controlling reduced pressure treatment systems, i.e., the pump pressure control, may vary depending on the magnitude of the pressure leaks or blockages and/or the rate of change of the pressure leaks or blockages. Consequently, the pump pressure control best suited for a high leak rate may be different from the pump pressure control best suited for a low leak rate. For example, a controller and control methods are described herein that include both PID and bang-bang controllers and an algorithm for switching between the two controls based on the level of leakage of components in the negative pressure system. The controller and control methods may select PID control for high leakage conditions and bang-bang control for low leakage conditions to conserve battery power and reduce noise from the pump. More specifically, the PID control might run constantly to maintain the pressure in a high leakage condition which would reduce battery power and expose the patient to the constant humming of the pump, while the bang-bang control might be sufficiently responsive in a low leakage condition which would conserve battery power and be less irritating because it would not need to be on all the time.

In one example embodiment, a system for stimulating healing of tissue at a wound site comprises a dressing including a porous pad and a drape covering the pad at a wound site for maintaining negative pressure at a wound site, a negative-pressure source including a pump and an electric motor to generate a pump pressure (PP) for applying to the wound site, and a first pressure sensor for sensing the pump pressure (PP). The system may further comprise a system controller coupled to the first pressure sensor and electric motor that may include a PID controller that operates continuously to maintain the wound pressure (WP) at a target one pressure (TP) and a bang-bang controller that is turned on and off to maintain the wound pressure (WP) within a range of pressures proximate the target wound pressure (TP). The system controller may be further configured to alternatively select the bang-bang controller when the system is in a low-leakage condition or the PID controller when the system is in a high-leakage condition.

In another example embodiment, a system for stimulating healing of tissue at a wound site comprises a dressing including a porous pad configured to be positioned and at the wound site and adapted to be covered by a drape to form a seal around the wound site for receiving negative pressure. The system further may further comprise a negative-pressure source including a pump fluidly coupled to the porous pad for applying a pump pressure (PP) to the wound site and an electric motor for driving the pump in response to the application of power, and a first pressure sensor having an input for sensing the pump pressure (PP) and an output for providing a pump pressure signal corresponding to the pump pressure (PP). The system may further comprise a system controller electrically coupled to the electric motor and the output of the first pressure sensor, the system controller being responsive to the pump pressure signal to control a wound pressure (WP) at the tissue site and configured to determine a flow rate (FR) of fluid between the pump and the porous pad. The system may further comprise a PID controller responsive to the system controller and configured to compare the pump pressure (PP) to a first set of minimum and maximum pump pressure values and vary the power applied to the electric motor in response to the comparison to maintain the wound pressure (WP) proximate a target pressure (TP). The system may further comprise a bang-bang controller responsive to the system controller and configured to compare the pump pressure (PP) to a second set of minimum and maximum pump pressure values and turn the electric motor on and off to maintain the wound pressure (WP) within a range of pressures from the target pressure (TP). The system controller may be further configured to engage the bang-bang controller if the flow rate (FR) is less than a first target flow rate (TFR1) and the PID controller if the flow rate (FR) is greater than the first target flow rate (TFR1).

Objectives, advantages, and a preferred mode of making and using the claimed subject matter may be understood best by reference to the accompanying drawings in conjunction with the following detailed description of illustrative embodiments.

DESCRIPTION OF EXAMPLE EMBODIMENTS

The following description of example embodiments provides information that enables a person skilled in the art to make and use the subject matter set forth in the appended claims, but may omit certain details already well-known in the art. The following detailed description is, therefore, to be taken as illustrative and not limiting.

The example embodiments may also be described herein with reference to spatial relationships between various elements or to the spatial orientation of various elements depicted in the attached drawings. In general, such relationships or orientation assume a frame of reference consistent with or relative to a patient in a position to receive treatment. However, as should be recognized by those skilled in the art, this frame of reference is merely a descriptive expedient rather than a strict prescription.

Figure 1:
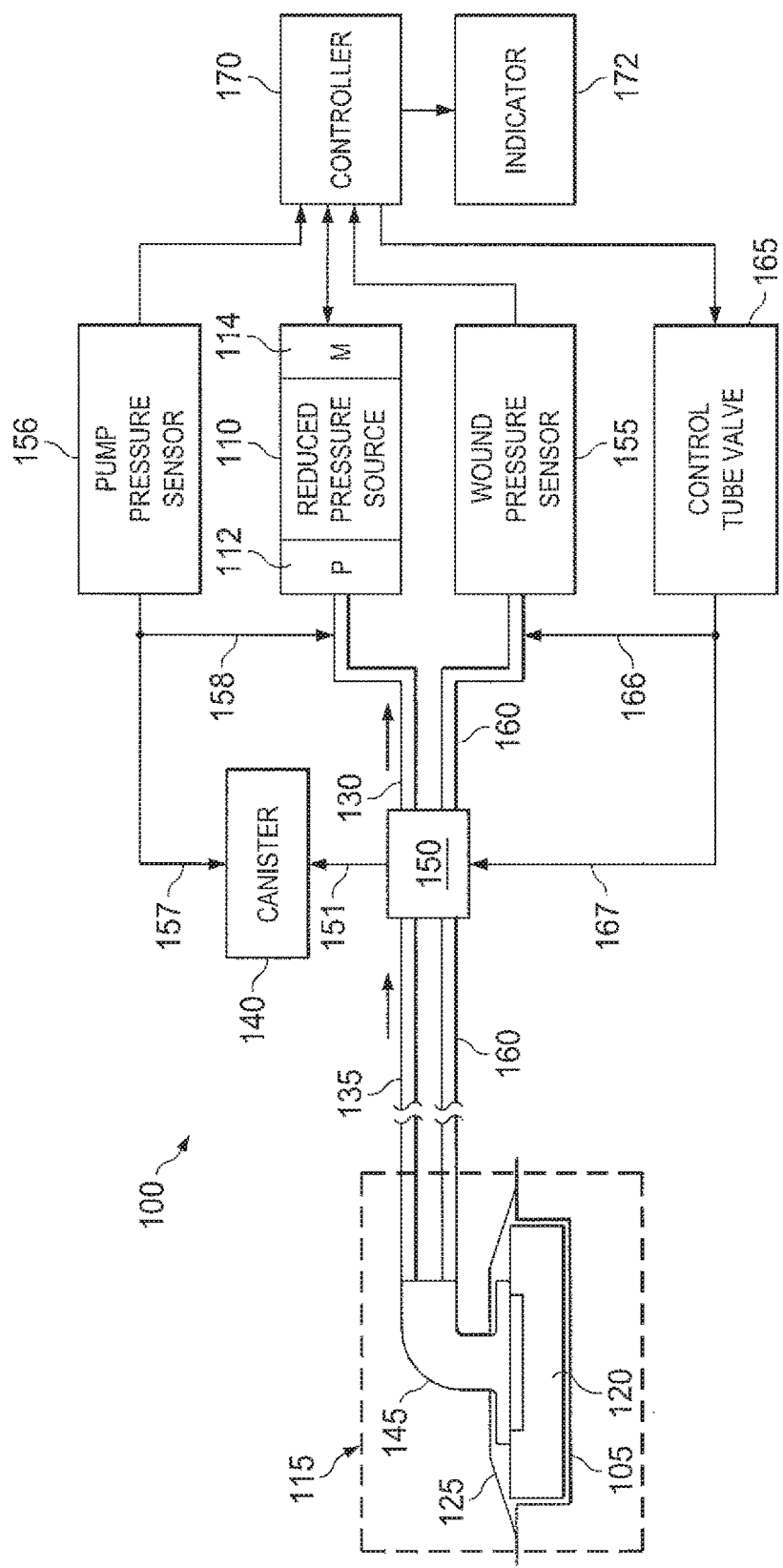
FIG. 1 is a functional block diagram of an embodiment of one example of a reduced-pressure therapy system including a controller coupled to a pump motor and a pump that can provide hybrid control of pressure being provided to a tissue site in accordance with this specification.

FIG. 1 is a simplified functional block diagram of an example embodiment of a reduced-pressure therapy system 100 that can provide negative-pressure therapy in accordance with this specification. More specifically, the therapy system 100 may be used for controlling which pump pressure control is utilized to provide the appropriate amount of reduced pressure to tissue site 105. Tissue site 105 may be the bodily tissue of any human, animal, or other organism, including bone tissue, adipose tissue, muscle tissue, dermal tissue, vascular tissue, connective tissue, cartilage, tendons, ligaments, or any other tissue. While tissue site 105 may include a wound, diseased tissue, or defective tissue, the tissue site may further include healthy tissue that is not wounded, diseased, or defective. The application of reduced pressure to tissue site 105 may be used to promote the drainage of exudate and other liquids from tissue site 105, as well as promote the growth of additional tissue. In the case in which tissue site 105 is a wound site, the growth of granulation tissue and removal of exudates and bacteria promotes healing of the wound. The application of reduced pressure to non-wounded or non-defective tissue, including healthy tissue, may be used to promote the growth of tissue that may be harvested and transplanted to another tissue location.

The reduced pressure applied to the tissue site 105 may be provided by a reduced pressure source 110. Reduced pressure source 110 may be any type of manually, mechanically, or electrically operated pump. Non-limiting examples of reduced pressure source 110 include devices that are driven by stored energy, and which are capable of producing a reduced pressure. Examples of these stored energy, reduced pressure sources include, without limitation, pumps driven by piezoelectric energy, spring energy, solar energy, kinetic energy, energy stored in capacitors, combustion, and energy developed by Sterling or similar cycles. Still other devices and processes that may be used or included in reduced pressure source 110 include syringes, lead screws, ratchets, clockwork-driven devices, pendulum-driven devices, manual generators, osmotic processes, thermal heating processes, and processes in which vacuum pressures are generated by condensation. In another embodiment, reduced pressure source 110 may include a pump 112 wherein the pump 112 provides negative or reduced pressure, i.e., a pump pressure (PP), to the tissue site 105 that may be driven by a motor 114 electrically coupled to a controller 170 which is also a component of the reduced-pressure therapy system 100, also referred to as a system controller. The motor 114 may be a direct-current motor powered by a DC power supply such as, for example, a battery (not shown). Preferably, the pump 112 uses low amounts of power and is capable of operating for an extended period of time on a single charge of the battery such as, for example, a diaphragm pump.

In one example embodiment, the reduced pressure source 110 comprises a DC motor 114 powered by a battery, i.e., the applied power. The applied power can be varied to control the speed of the motor by varying either the current or the voltage applied to the motor, i.e., the "applied voltage" ($V_A$). The applied voltage ($V_A$) may be varied, for example, by modulating the voltage with a square wave and varying the duty cycle of the square wave to control the speed of the DC motor 114. The reduced pressure source 110 also comprises a pump 112 that provides a reduced pressure or vacuum to the tissue site 105. Consequently, the pump 112 represents the load on the DC motor 114 so that when the therapy requires that the reduced pressure at the tissue site 105 needs to be increased, the applied voltage ($V_A$) provided to the DC motor 114 is increased to achieve the targeted reduced pressure at the tissue site 105. One skilled in the art knows that the DC motor 114 will not run or turn the pump until the applied voltage ($V_A$) is sufficient to overcome the inertia or load of the pump 112, which in this case may be a diaphragm pump.

Figure 2:
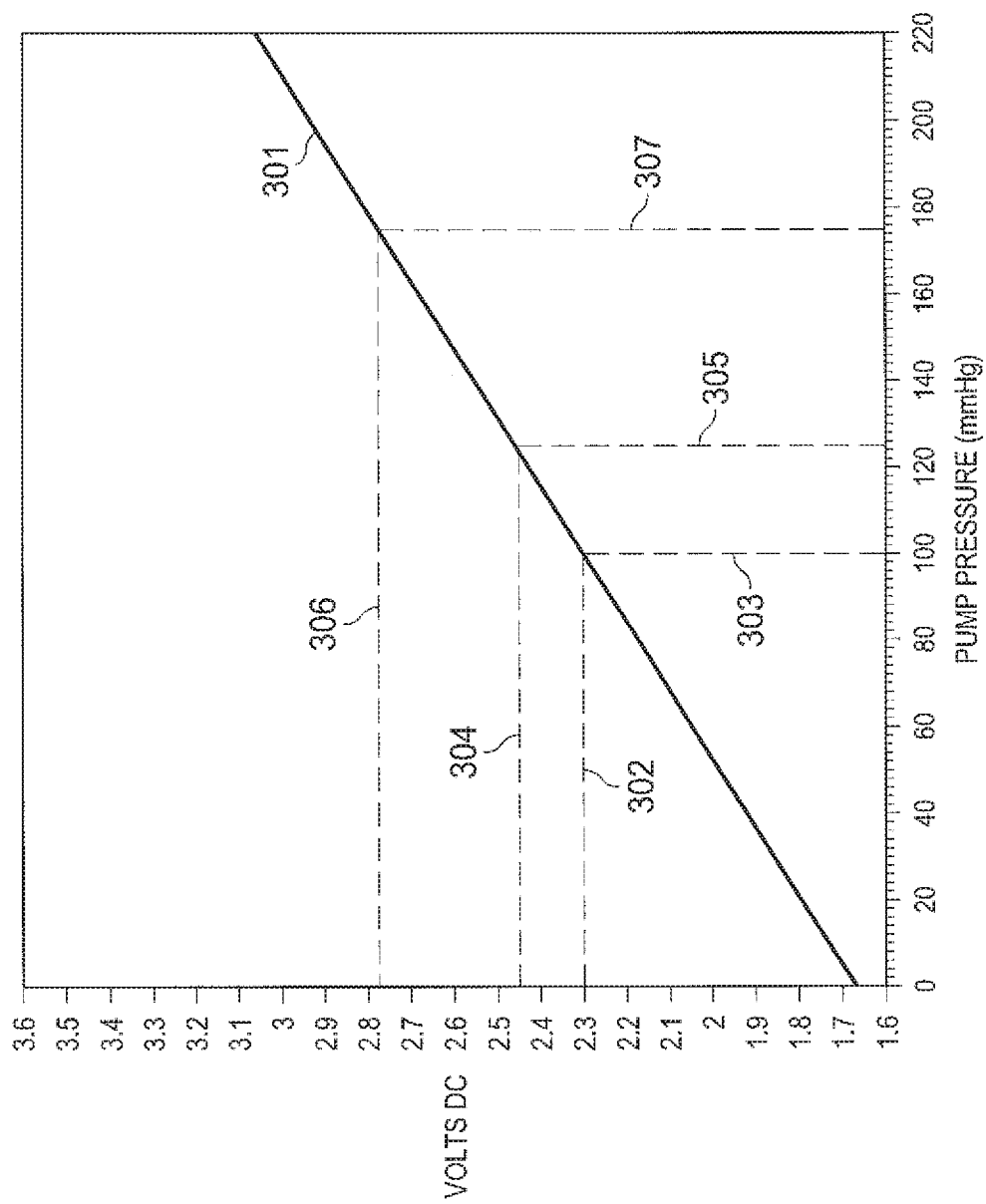
FIG. 2 is a graph illustrating stall voltage characteristics for a pump motor that may be used in the reduced pressure therapy system of FIG. 1 wherein the x-axis represents the vacuum pressure loading for the pump motor and the y-access represents the stall voltage.

Referring more specifically to FIG. 2, a graph 301 illustrating the voltages for the pump motor 114 necessary to start the pump 112 is shown wherein the X-axis represents the pump pressure (PP) loading the DC pump motor and the Y-axis represents the applied voltage ($V_A$). For example, the controller 170 may need to apply at least 2.3V to the DC motor 114 before it will turn the pump 112 when loaded at a pressure of 100 mmHg as indicated by the dashed lines 302, 303. Applying any less than 2.3V to the DC motor 114 would yield insufficient power for the motor to turn the pump, i.e., the loaded motor would remain stopped or "stalled" so that the motor is unable to turn the pump. Hence, the 2.3V value is often referred to in the industry as the "stall voltage" that would be calculated for a DC motor under a load of 100 mmHg of pressure, i.e., the "stall pressure." Correspondingly, the controller 170 may need to apply a larger voltage of at least 2.45V 304 to the DC motor before it will turn the pump when loaded at a greater pressure of 125 mmHg 305. Applying any less than the stall voltage of 2.45V to the DC motor would not be sufficient to cause the DC motor to turn the pump under a stall pressure of 125 mmHg. Variations in the stall voltage are proportional to the variations in the pressure load on the motor, i.e., the greater the pressure load is on the motor, the greater the stall voltage needed to overcome the pressure load.

The specific stall voltage for a specific DC motor used to drive a diaphragm pump can typically be determined by one skilled in the art from the specifications available for the DC motor. The diaphragm pump and DC motor may be and integrated device such as, for example, a Thomas Model No. 30130002 series 4.5V diaphragm pump for which such information is readily available. (Thomas; thomas.de@gardnerdenver.com) Referring again to FIG. 2, the graph 301 illustrating the stall voltage for the pump motor, the Y-axis represents the stall voltages calculated for this Thomas motor based on the specifications presently available at the Thomas website referred to above. The examples provided in the paragraph above include voltages and pressures that are exemplary only. The graph 301 simply illustrates that one skilled in the art can calculate the various stall voltages for a DC motor based on specifications typically available for that motor. Those working with miniature diaphragm pumps that are driven by a DC motor, such as the Thomas DC motor, often refer to the stall voltage as the "stall power", i.e., the product of the stall voltage and the rated current of the specific DC motor.

Data from pump specifications is typically limited to the relation of maximum flow to vacuum pressure at maximum pump voltage (e.g., 4.5V for Thomas pump identified above). Positive pressures are specified in mbar units (mmHg of positive pressure=0.7500616827042*mbars) and vacuum pressures are specified in terms of percent vacuum. For example, if 100% maximum vacuum is specified at 760 mmHg, 40% maximum vacuum would be equal to 304 mmHg of vacuum (=0.4*760 mmHg). In this example, the 304 mmHg of vacuum pressure would be the theoretical maximum vacuum pressure that we could attain if the pump was run at 4.5V and allowed to run until it the DC motor stalls. The graph 301 in FIG. 2 was generated based on the motor specifications and the stall voltages observed that were needed to drive this pump.

The equation for calculating the stall voltage for this particular pump is as follows: Stall Voltage=1.638V+ (0.006515V/mmHg*XmmHg), where X is the current vacuum pressure. Therefore, at 50 mmHg of vacuum, the stall voltage equals 1.96V (1.638+(0.006515*50)); at 125 mmHg of vacuum, the stall voltage equals 2.45V (1.638+ (0.006515*125)) as indicated by the dashed lines 304, 305; and at 175 mmHg of vacuum, the stall voltage equals 2.78V (1.638+(0.006515*175)) as indicated by the dashed lines 306, 307. Again, the higher the vacuum pressure, the higher the applied voltage that is needed to start the pump. Otherwise, the pump stalls and will not move until the necessary stall will voltage is applied. When the pump stalls, the DC motor simply overheats which can damage the DC motor and reduce battery life.

Referring back to FIG. 1, the reduced pressure source 110 may provide reduced pressure to the tissue site 105 via a dressing 115. Dressing 115 may include a tissue interface such as, for example, a manifold 120 which may be placed adjacent to or in contact with the tissue site 105. Manifold 120 may be a biocompatible, porous material that is capable of being placed in contact with tissue site 105 and distributing reduced pressure to the tissue site 105. Manifold 120 may be made from foam, gauze, felted mat, or any other material suited to a particular biological application. Manifold 120 may include a plurality of flow channels or pathways to facilitate distribution of reduced pressure or fluids to or from tissue site 105.

In one embodiment, manifold 120 is a porous foam and includes a plurality of interconnected cells or pores that act as flow channels. The porous foam may be a polyurethane, open-cell, reticulated foam such as GranuFoam manufactured by Kinetic Concepts, Inc. of San Antonio, Tex. If an open-cell foam is used, the porosity may vary, but is preferably about 400 to 600 microns. The flow channels allow fluid communication throughout the portion of manifold 120 having open cells. The cells and flow channels may be uniform in shape and size, or may include patterned or random variations in shape and size. Variations in shape and size of the cells of manifold result in variations in the flow channels, and such characteristics may be used to alter the flow characteristics of fluid through manifold 120. The manifold 120 may further include portions that include "closed cells." These closed-cells portions of manifold 120 contain a plurality of cells, the majority of which are not fluidly connected to adjacent cells. Closed-cell portions may be selectively disposed in manifold 120 to prevent transmission of fluids through perimeter surfaces of manifold 120.

Manifold 120 may also be constructed from bioresorbable materials that do not have to be removed from a patient's body following use of reduced pressure treatment system 100. Suitable bioresorbable materials may include, without limitation, a polymeric blend of polylactic acid (PLA) and polyglycolic acid (PGA). The polymeric blend may also include without limitation polycarbonates, polyfumarates, and capralactones. Manifold 120 may further serve as a scaffold for new cell-growth, or a scaffold material may be used in conjunction with manifold 120 to promote cell-growth. A scaffold is a substance or structure used to enhance or promote the growth of cells or formation of tissue, such as a three-dimensional porous structure that provides a template for cell growth. Illustrative examples of scaffold materials include calcium phosphate, collagen, PLA/PGA, coral hydroxy apatites, carbonates, or processed allograft materials. In one example, the scaffold material has a high void-friction (i.e., a high content of air).

The dressing 115 may also include sealing member 125 also referred to as a drape or cover. Manifold 120 may be secured to tissue site 105 using sealing member 125. Sealing member 125 may be a cover that is used to secure manifold 120 at tissue site 105. While sealing member 125 may be impermeable or semi-permeable, in one example sealing member 125 is capable of maintaining a reduced pressure at tissue site 105 after installation of the sealing member 125 over manifold 120. Sealing member 125 may be a flexible drape or film made from a silicone based compound, acrylic, hydrogel or hydrogel-foaming material, or any other biocompatible material that includes the impermeability or permeability characteristics desired for tissue site 105. Sealing member 125 may be formed of a hydrophobic material to prevent moisture absorption by the sealing member 125. In one embodiment, sealing member 125 is configured to provide a sealed connection with the tissue surrounding manifold 120 and tissue site 105. The sealed connection may be provided by an adhesive (not shown) positioned along a perimeter of sealing member 125 or on any portion of sealing member 125 to secure sealing member 125 to the manifold 120 or the undamaged epidermis peripheral to a tissue site, i.e., the peritissue. The adhesive may be pre-positioned on sealing member 125 or may be sprayed or otherwise applied to sealing member 125 immediately prior to installing sealing member 125.

In general, components of the therapy system 100 may be coupled directly or indirectly. Components may be fluidly coupled to each other to provide a path for transferring fluids (i.e., liquid and/or gas) between the components. In some embodiments, for example, components may be fluidly coupled through a tube. A "tube," as used herein, broadly refers to a tube, pipe, hose, conduit, or other structure with one or more lumina adapted to convey a fluid between two ends. Typically, a tube is an elongated, cylindrical structure with some flexibility, but the geometry and rigidity may vary. In some embodiments, components may additionally or alternatively be coupled by virtue of physical proximity, being integral to a single structure, or being formed from the same piece of material. Coupling may also include mechanical, thermal, electrical, or chemical coupling (such as a chemical bond) in some contexts The reduced pressure generated by reduced pressure source 110 may be applied to tissue site 105 through source tube 130 and delivery tube 135. Source tube 130 and delivery tube 135 may be any tube through which a gas, liquid, gel, or other fluid may flow. For example, exudate from tissue site 105 may flow through delivery tube 135. In FIG. 1, source tube 130 couples reduced pressure source 110 to a canister 140 and delivery tube 135 couples the canister 140 to the dressing 115. However, in another embodiment, reduced pressure source 135 may be directly coupled to dressing 115 using delivery tube 135.

Source tube 130 and delivery tube 135 may be made from any material. Source tube 130 and delivery tube 135 may be either flexible or inflexible. Also, source tube 130 and delivery tube 135 may include one or more paths or lumens through which fluid may flow. For example, delivery tube 135 may include two lumens. In this example, one lumen may be used for the passage of exudate from tissue site 105 to canister 140. The other lumen may be used to deliver fluids, such as air, antibacterial agents, antiviral agents, cell-growth promotion agents, irrigation fluids, or other chemically active agents, to tissue site 105. The fluid source from which these fluids originate is not shown in FIG. 1. Additional details regarding the inclusion of multi-lumen tubes in reduced pressure treatment system 100 are provided below.

In one embodiment, delivery tube 135 is coupled to manifold 120 via connection member 145. Connection member 145 permits the passage of fluid from manifold 120 to delivery tube 135, and vice versa. For example, exudates collected from tissue site 105 using manifold 120 may enter delivery tube 135 via connection member 145. In another embodiment, reduced pressure treatment system 100 does not include connection member 145. In this embodiment, delivery tube 135 may be inserted directly into sealing member 125 or manifold 120 such that an end of delivery tube 135 is adjacent to or in contact with manifold 120.

Liquid, such as exudate, from tissue site 105 may flow through delivery tube 135 into canister 140. Canister 140 may be any device or cavity capable of containing a fluid, such as gases and liquids, as well as fluids that contain solids. For example, canister 140 may contain exudates from tissue site 105. Source tube 130 and delivery tube 135 may be directly connected to canister 140, or may be coupled to canister 140 via a connector, such as connector 150, as indicated by arrow 151. The canister 140 may be a flexible or rigid canister, a bag, or pouch fluidly connected to manifold 120 by delivery tube 135. Canister 140 may be a separate canister or may be operably combined with reduced pressure source 110 to collect exudate and fluids.

Reduced pressure treatment system 100 may further comprise a first pressure sensor 155 electrically coupled to the controller 170. Pressure sensor 155 detects an actual reduced pressure at or proximate the tissue site 105, i.e., the tissue site pressure or wound pressure (WP). The reference to the word "wound" as part of the term wound pressure (WP) is exemplary only and does not limit the term or description herein as applying to the measurement of pressure at other types of tissue sites such as, for example, incisions or subcutaneous cavities. In one non-limiting example, pressure sensor 155 is a silicon piezo-resistive gauge pressure sensor. Pressure sensor 155 may be configured to detect the wound pressure (WP) via a control tube 160 fluidly coupled to the connection member 145 or via one of the lumens of the delivery to 135 as described above through the connector 150. Control tube 160 is any tube through which a gas may flow. Control tube 160 may be made from any material. Control tube 160 may be either flexible or inflexible. Also, control tube 160 may include one or more paths or lumens through which fluid may flow.

Reduced pressure treatment system 100 may further comprise a second pressure sensor 156 electrically coupled to the controller 170. Pressure sensor 156 detects a reduced pressure at or downstream from the canister 140 indicated by arrows 157 and 158, respectively, i.e., the pump pressure (PP). In one non-limiting example, pressure sensor 156 is a silicon piezo-resistive gauge pressure sensor. The pressure sensor 156 may be fluidly coupled directly to the canister 144 or the source tube 130, or indirectly via a control tube (not shown) as indicated by the arrows 157 and 158, to detect the pump pressure (PP). The pressure sensor 156 may also be fluidly coupled to the canister 144 through the connector 150.

In FIG. 1, control tube 160 is shown as passing through connector 150. However, the placement of control tube 160 may be varied to accommodate particular needs and applications. For example, control tube 160 may be routed through canister 140, along an outside surface of canister 140, or may bypass canister 140. The end of control tube 160 that is opposite of pressure sensor 155 may be coupled to manifold 120 via the connection member 145. In another example, control tube 160 may be inserted directly into sealing member 125 or manifold 120 such that an end of control tube 160 is adjacent to or in contact with manifold 120.

Figure 1A:
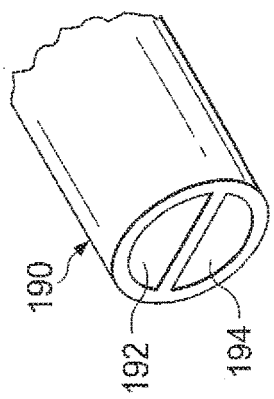
FIG. 1A is a perspective view of a multi-lumen tube that may be used in the reduced pressure therapy system of FIG. 1 in accordance with an illustrative embodiment of the invention.

In another embodiment, delivery tube 135 and control tube 160 are each lumens in a single multi-lumen tube. Source tube 130 and control tube 160 may also each be lumens in a single multi-lumen tube. In the example in which reduced pressure source 110 is coupled to manifold 120 using only delivery tube 135, a single multi-lumen tube may be used to couple both reduced pressure source 110 and pressure sensor 155 to manifold 120. Turning to FIG. 1A, a perspective view of a multi-lumen tube is depicted in accordance with an illustrative embodiment of the present invention. Specifically, FIG. 1A depicts multi-lumen tube 190, which may be implemented in a reduced pressure treatment system, such as reduced pressure treatment system 100 in FIG. 1.

Multi-lumen tube 190 includes two lumens. Specifically, multi-lumen tube 190 includes lumens 192 and 194. Although multi-lumen tube 190 includes two lumens 192 and 194, multi-lumen tube may have any number of lumens, such as three, four, or ten. In one embodiment, one of lumens 192 and 194, such as lumen 192, is a delivery tube or source tube, such as delivery tube 135 and source tube 130 in FIG. 1. In another embodiment, one of lumens 192 and 194, such as lumen 194, is a control tube, such as control tube 160 in FIG. 1. By incorporating a combination of a delivery tube, source tube, and control tube as lumens in a single multi-lumen tube, the number of separate tubes included in the reduced pressure treatment system may be reduced. The reduced number of tubes simplifies the reduced pressure treatment system for use by a user, and lessens the burden of carrying the reduced pressure treatment system.

Pressure sensors 155 and 156 may be located anywhere on or within the reduced pressure treatment system 100. Referring back to FIG. 1, pressure sensor 155 is shown to be remote from tissue site 105. In this example, the reduced pressure at tissue site 105 may be detected from remotely located pressure sensor 155 through the control tube 160, which permits the flow of gas. Also in this example, pressure sensor 156 may be directly or indirectly coupled to other remotely located components of reduced pressure treatment system 100, such as reduced pressure source 110, the canister 140, or any other illustrated component of reduced pressure treatment system 100. In another example, pressure sensor 155 may not require the use of control tube 160 to detect the pressure at tissue site 105. In one non-limiting example, pressure sensor 155 is directly coupled to manifold 120 or placed between sealing member 125 and manifold 120.

Reduced pressure treatment system 100 may also include control tube valve 165. Control tube valve 165 may be coupled to control tube 160 as indicated by arrow 166 or indirectly coupled to the source tube 134 or the canister 140 as indicated by arrow 168. Control tube valve 165 may be any valve capable of relieving the reduced pressure in control tube 160. Non-limiting examples of control tube valve 165 include a pneumatic solenoid valve, a proportional valve, or a mechanical valve. In one example, control tube valve 165 may be manually controlled by a caregiver. In another example, control tube valve 165 may be controlled by a controller. In one embodiment, control tube valve 165 may be opened to relieve the reduced pressure in control tube 160 or the source tube 130 when a blockage is detected in either one. Such a blockage may occur, for example, when exudate or other fluid from tissue site 105 clogs control tube 160 or the source tube 130. By relieving the reduced pressure in control tube 160 or the source tube 130 via control tube valve 165, the blockage may be cleared from either one.

In operation, the manifold 120 may be placed within, over, on, or otherwise proximate to a tissue site. The sealing member 125 may be placed over the manifold 120 and sealed to tissue near the tissue site 105. For example, the sealing member 125 may be sealed to undamaged epidermis peripheral to a tissue site, i.e., the peritissue. Thus, the dressing 115 can provide a sealed therapeutic environment proximate to a tissue site, substantially isolated from the external environment, and the reduced pressure source 110 can reduce the pressure in the sealed therapeutic environment. Reduced pressure applied across the tissue site through the manifold 120 in the sealed therapeutic environment can induce macrostrain and microstrain in the tissue site, as well as remove exudates and other fluids from the tissue site, which can be collected in the canister 140 and disposed of properly.

The fluid mechanics of using a reduced-pressure source to reduce pressure in another component or location, such as within a sealed therapeutic environment, can be mathematically complex. However, the basic principles of fluid mechanics applicable to negative-pressure therapy are generally well-known to those skilled in the art, and the process of reducing pressure may be described illustratively herein as "delivering," "distributing," or "generating" negative pressure, for example.

In general, exudates and other fluids flow toward lower pressure along a fluid path. Thus, the term "downstream" typically implies something in a fluid path relatively closer to a reduced-pressure source, and conversely, the term "upstream" implies something relatively further away from a negative-pressure source. Similarly, it may be convenient to describe certain features in terms of fluid "inlet" or "outlet" in such a frame of reference. This orientation is generally presumed for purposes of describing various features and components of reduced-pressure therapy systems herein. However, the fluid path may also be reversed in some applications (such as by substituting a positive-pressure source for a reduced-pressure source) and this descriptive convention should not be construed as a limiting convention.

The term "tissue site" in this context broadly refers to a wound or defect located on or within tissue, including but not limited to, bone tissue, adipose tissue, muscle tissue, neural tissue, dermal tissue, vascular tissue, connective tissue, cartilage, tendons, or ligaments. A wound may include chronic, acute, traumatic, subacute, and dehisced wounds, partial-thickness burns, ulcers (such as diabetic, pressure, or venous insufficiency ulcers), flaps, and grafts, for example. The term "tissue site" may also refer to areas of any tissue that are not necessarily wounded or defective, but are instead areas in which it may be desirable to add or promote the growth of additional tissue. For example, negative pressure may be used in certain tissue areas to grow additional tissue that may be harvested and transplanted to another tissue location.

"Negative or reduced pressure" generally refers to a pressure less than a local ambient pressure, such as the ambient pressure in a local environment external to a sealed therapeutic environment provided by the dressing 102. In many cases, the local ambient pressure may also be the atmospheric pressure at which a tissue site is located. Alternatively, the pressure may be less than a hydrostatic pressure associated with tissue at the tissue site. Unless otherwise indicated, values of pressure stated herein are gauge pressures. Similarly, references to increases in negative pressure typically refer to a decrease in absolute pressure, while decreases in negative pressure typically refer to an increase in absolute pressure.

A negative-pressure source, such as the reduced pressure source 110, may be a reservoir of air at a reduced pressure, or may be a manual or electrically-powered device that can reduce the pressure in a sealed volume, such as a vacuum pump, a suction pump, a wall suction port available at many healthcare facilities, or a micro-pump, for example. A negative-pressure source may be housed within or used in conjunction with other components, such as processing units, alarm indicators, memory, databases, software, display devices, or user interfaces that further facilitate negative-pressure therapy. For example, the reduced pressure source 110 and the controller 106 may be housed within a therapy control unit. While the amount and nature of negative pressure applied to a tissue site may vary according to therapeutic requirements, the pressure is generally a low vacuum, also commonly referred to as a rough vacuum, between −5 mm Hg (−667 Pa) and −500 mm Hg (−66.7 kPa). Common therapeutic ranges are between −75 mm Hg (−9.9 kPa) and −300 mm Hg (−39.9 kPa).

As indicated above, the applied voltage ($V_A$) provided to the DC motor 114 is used to control the pump pressure (PP) and ultimately achieve the desired or targeted pressure at the tissue site 105. Correspondingly, the applied voltage ($V_A$) provides an indication of the pump pressure (PP) and may be monitored by the controller 170 which in turn may determine the time rate of change of the applied voltage ($V_A$) that necessarily corresponds to the time rate of change of the pump pressure (PP). The controller 170 may use this computation for determining the flow rate of air between the reduced pressure source 110 and tissue site 105, i.e., the flow rate (FR). In another embodiment, the reduced pressure treatment system 100 may further comprise a sensing device (not shown) that directly measures the flow rate (FR) such as, for example, a flow-meter or a differential processor for computing the time rate of change in the difference between the wound pressure (WP) and the pump pressure (PP). The flow rate (FR) may be measured, for example, as cubic centimeters of air per minute (cc/min), between the reduced pressure source 110 and the tissue site 105. The flow rate (FR) provides some indication of the extent to which the dressing 115 or other components of the negative pressure system 100 might be leaking to reduce the pressure at the tissue site 105 below the desired pressure targeted for therapy. For example, a high flow rate (FR) might indicate that the dressing 115 or other components of the system 100 are considered to be in a "high leakage condition," while a lower flow rate (FR) might indicate that the dressing 115 or other components of the system 100 are considered to be in a more efficient "low leakage condition" requiring less battery power for driving the DC motor 114 to continue running in order to offset the higher leakage.

The controller 170 may be an integrated or separate component of the reduced-pressure treatment system 100. Controller 170 may be any device capable of processing data, such as data from pressure sensor 155 and/or the pressure sensor 156. Controller 170 may also control the operation of one or more components of reduced pressure treatment system 100, such as reduced pressure source 110, motor 114, control tube valve 165, pressure sensors 155 and 156, and indicator 172. The controller 170 may control and receive data from other components (not shown) of the reduced pressure source 110 including the pump 112 and the motor 114. In one embodiment, controller 170 receives and processes data, such as the wound pressure (WP) from the pressure sensor 155, the pump pressure (PP) from the pressure sensor 156, and the flow rate (FR) from monitoring the applied voltage ($V_A$) to the motor 114 as described above. The controller 170 may also control the operation of one or more components of reduced pressure treatment system 100 to manage the wound pressure (WP) at tissue site 105. In one embodiment, controller 170 may including an input for receiving a desired target pressure (TP) set by a clinician or other user and may be program for processing data relating to the setting and inputting of the target pressure (TP) to be applied to the tissue site 105.

In one example embodiment, the target pressure (TP) may be a fixed pressure value determined by a user/caregiver as the reduced pressure target desired for therapy at the tissue site 105 and then provided as input to the controller 110. The user may be a nurse or a doctor or other approved clinician who prescribes the desired reduced pressure to which the tissue site 105 should be applied. The desired tissue site pressure will vary from tissue site to tissue site, but will generally be chosen based on the type of tissue making up the tissue site, the type of injury or wound (if any), the medical condition of the patient, and the preference of the attending physician. After selecting the desired target pressure (TP), the reduced pressure source 110 is controlled to achieve the target pressure (TP) desired for application to the tissue site 105.

Figure 3:
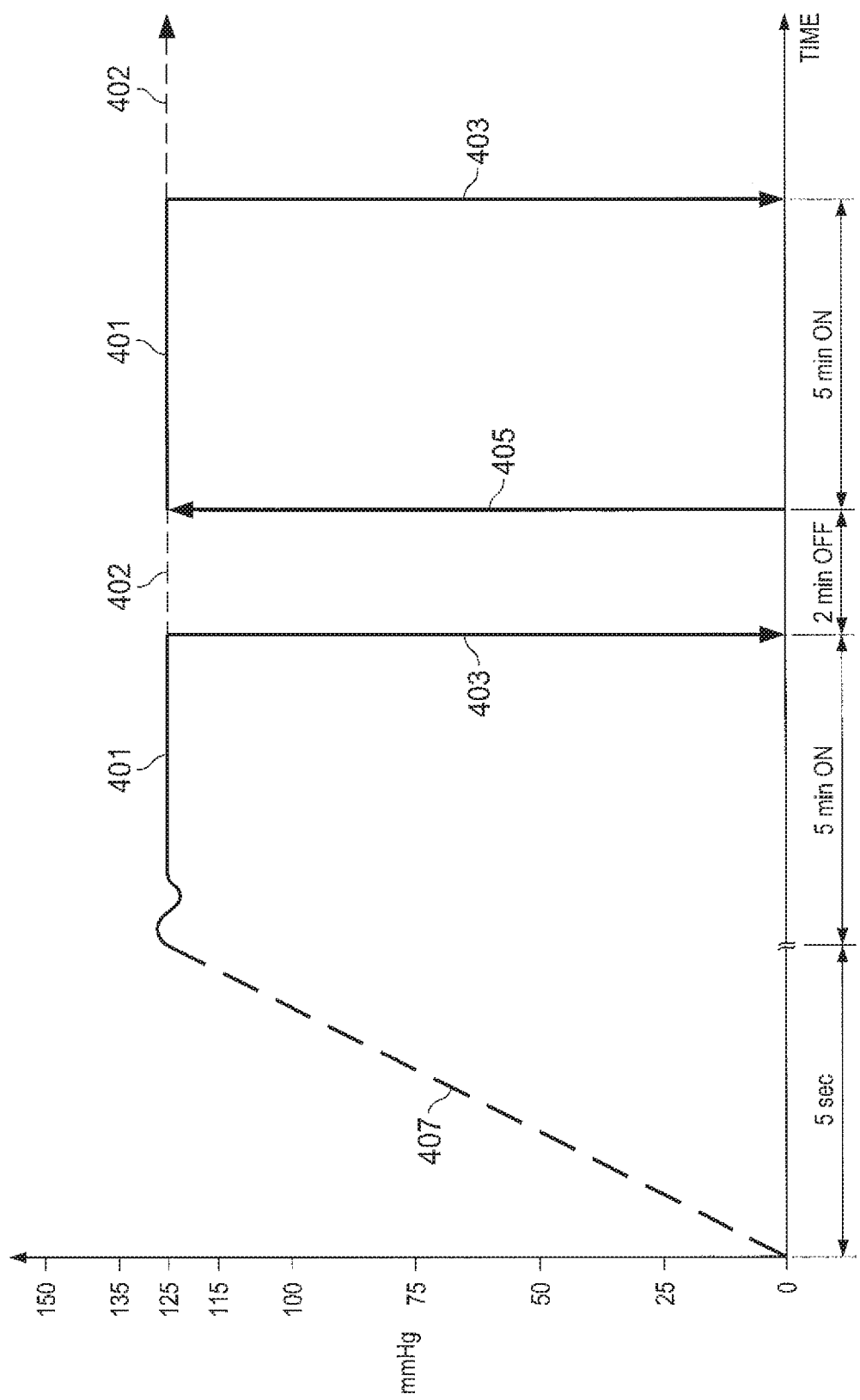
FIG. 3 is a graph illustrating pressure control of a motor-drive system in accordance with an illustrative embodiment of the example embodiment wherein the x-axis represents time in minutes (min) and/or seconds (sec) and the y-axis represents pressure generated by a pump in Torr (mmHg) that varies with time in a continuous control mode and an intermittent mode that may be used in the reduced pressure therapy system of FIG. 1.

Referring more specifically to FIG. 3, the target pressure (TP) may be set by the user in a continuous mode as indicated by solid line 401 and dotted line 402 wherein the wound pressure (WP) is applied to the tissue site 105 until the user deactivates the reduced pressure source 110. The target pressure (TP) may also be set by the user in an intermittent mode as indicated by solid lines 401, 403 and

405 wherein the wound pressure (WP) is cycled between the target pressure (TP) and atmospheric pressure. For example, the target pressure (TP) may be set by the user at 125 mmHg for a specified period of time (e.g., 5 min) followed by the therapy being turned off for a specified period of time (e.g., 2 min) as indicated by lines 403 by venting the tissue site 105 to the atmosphere, and then repeating the cycle by turning the therapy back on as indicated by line 405 which consequently forms a square wave pattern between the target pressure (TP) level and no pressure.

It should be understood that the increase of the wound pressure (WP) at the tissue site 105 from ambient pressure to the target pressure (TP) is not instantaneous, but rather limited depending on the type of therapy equipment and the dressing. For example, the reduced pressure source 110 and the dressing 115 may have an initial rise time as indicated by the dashed line 407 that may vary depending on the type of dressing and therapy equipment being used. For example, the initial rise time for one therapy system may be in the range between about 20-30 mmHg/second or, more specifically, equal to about 25 mmHg/second, and in the range between about 5-10 mmHg/second for another therapy system. When the therapy system is operating in the intermittent mode, the repeating rise time 405 may be a value substantially equal to the initial rise time 407.

The target pressure may also be a variable target pressure (VTP) controlled or determined by controller 170 that varies in a dynamic pressure mode. For example, the variable target pressure (VTP) may vary between a maximum and minimum pressure value that may be set as an input by a user as the range of reduced pressures desired for therapy at the tissue site 105. The variable target pressure (VTP) may also be processed and controlled by controller 170 that varies the target pressure (TP) according to a predetermined waveform such as, for example, a sine waveform or a saw-tooth waveform or a triangular waveform, that may be set as an input by a user as the predetermined or time-varying reduced pressures desired for therapy at the tissue site 105. For example, the variable target pressure (VTP) may be a reduced pressure that provides an effective treatment by applying reduced pressure to tissue site 105 in the form of a triangular waveform varying between 50-125 mmHg with a rise time set at +25 mmHg/min and a descent time set at −25 mmHg/min. In another embodiment of a reduced-pressure therapy system 100, the variable target pressure (VTP) may be a reduced pressure that applies reduced pressure to tissue site 105 in the form of a triangular waveform varying between 25-125 mmHg with a rise time set at a rate of +30 mmHg/min and a descent time set at −30 mmHg/min. Again, the type of system and tissue site determines the type of reduced pressure therapy to be used.

After selecting the target pressure (TP), the reduced pressure source 104 is operated to achieve the desired pressure at the wound site 105 by controlling pressure (PP). In many cases, the reduced pressure source 110 to be operated at a higher pump pressure (PP) than that of the target pressure (TP) due to pressure losses between the reduced pressure source 110 and the tissue site 105. Moreover, the head pressure of exudates and other fluids within the conduits may result in a reduction of vacuum pressure at the tissue site 105. The height of the canister 140 above the tissue site 105 may determine the amount of head pressure imposed on the tissue site 105 by fluid in the conduits. For exudates and fluids with a density similar to water, the head pressure imposed by one foot of fluid is almost 25 mmHg. Some fluids withdrawn from the tissue site 105 may be even heavier or more viscous than water, and therefore have a more pronounced effect on pressure losses at the tissue site 105.

Figure 4:
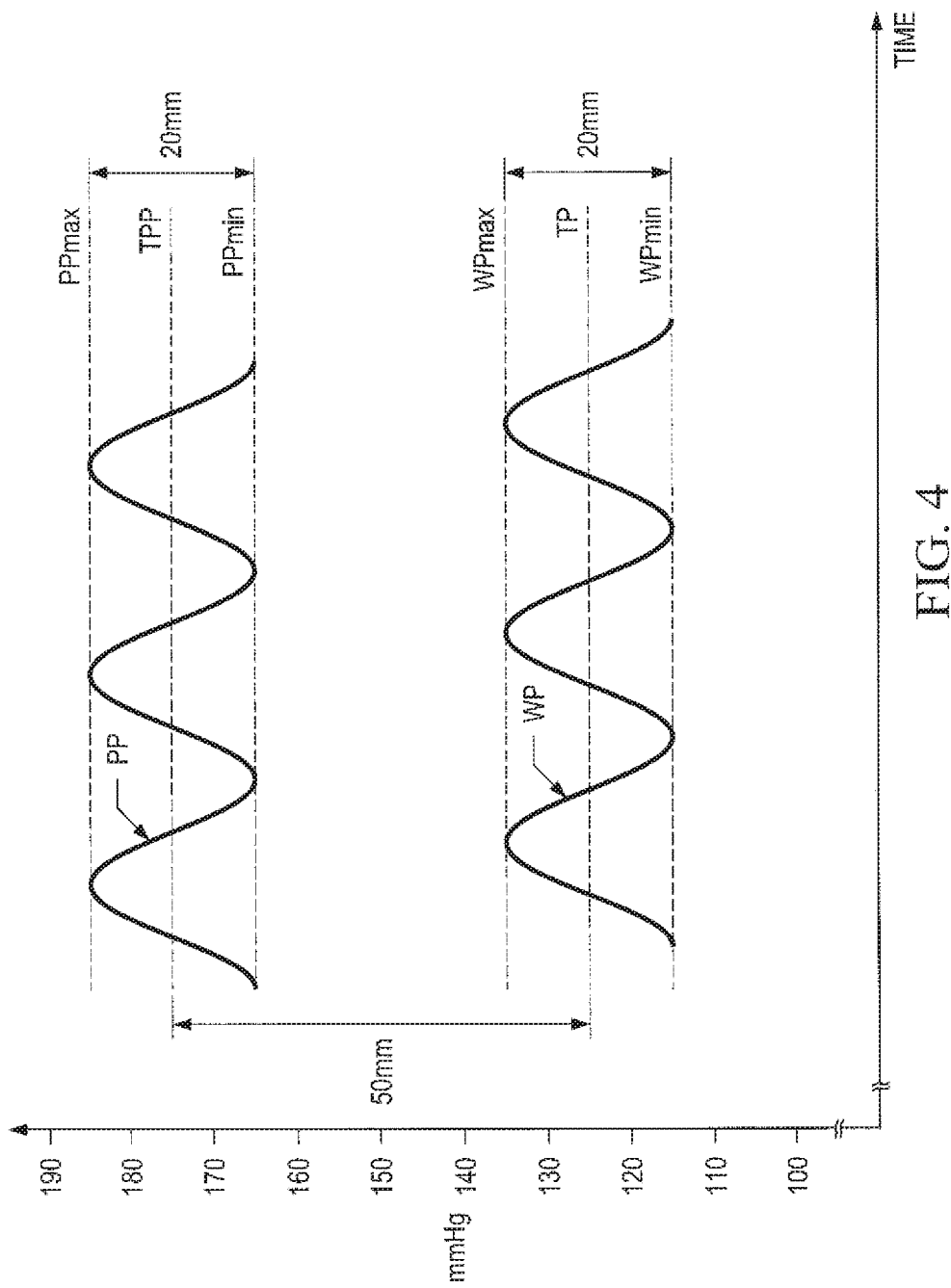
FIG. 4 is a graph illustrating pressure control of a motor-drive system in accordance with an illustrative embodiment of the example embodiment wherein the x-axis represents time in minutes (min) and/or seconds (sec) and the y-axis represents pressure generated by a pump in Torr (mmHg) that compares a manipulated variable, i.e., a tissue site or wound pressure (WP) at a tissue site, and a control variable, i.e., a pump pressure (PP), for use with a PID controller and/or a bang-bang controller.

Referring to FIG. 4 as an example of the potential losses caused by the weight of fluid in the conduits, the target pressure (TP) prescribed for a particular tissue site may be −125 mm Hg wherein the wound pressure (WP) varies as the reduced pressure is applied to the tissue site 105. (It should be understood that the steady sinusoidal variations of the wound pressure (WP) shown in FIG. 4 are only explanatory and not representative of the actual variations of the wound pressure (WP) under normal operational conditions such as, for example, the variations shown in FIGS. 5, 5A and 5B.) If the canister 140 is positioned two feet above the tissue site 105, and if the delivery tube 135 between the canister 140 and tissue site 105 is completely full of fluid, the head pressure imposed by that fluid could create a pressure differential ($\delta P$) of approximately 50 mmHg as shown in FIG. 4. This particular example occurs when a tissue site is located on a lower extremity of a patient such as a foot and the canister 140 is mounted near or above the patient's head (e.g., on an IV pole when the patient is in a wheelchair). Therefore, if the head pressure of fluid in the delivery tube 135 is approximately 50 mmHg, the pump 112 needs to provide a pump pressure (PP) rising to a maximum pump pressure value (PPmax) of approximately 185 mmHg and dropping to a minimum pump pressure value (PPmin) of approximately 165 mmHg (a median target pump pressure (TPP) of approximately 175 mmHg) to yield a target pressure (TP) at the tissue site 105 of approximately 125 mmHg.

The controller 110 may also be programmed and controlled by a user to maintain the target pressure (TP) within an acceptable range of pressures. For example, if the target pressure (TP) is set at 125 mmHg as the desired therapeutic pressure for the tissue site 105, a user may desire that the wound pressure (WP) varies by no more than ±10 mmHg from the desired target pressure (TP) so that the wound pressure (WP) is controlled between a minimum wound pressure value (WPmin) of 115 mmHg and a maximum wound pressure value (WPmax) of 135 mmHg, i.e., a differential wound pressure range ($\delta WP$) of about 20 mmHg. Therefore, assuming for this example that there is a head pressure approximately 50 mmHg as described above, the pump pressure (PP) must also be variable by ±10 mmHg from the target pump pressure (TPP) so that the pump pressure (PP) may be varied in a range extending from the minimum pump pressure value (PPmin) of approximately 165 mmHg to the maximum pump pressure value (PPmax) of approximately 185 mmHg, i.e., a differential pump pressure ($\delta TTP$) of about 20 mmHg. Controlling the pump pressure (PP) to stay within this range indirectly maintains the wound pressure (WP) within a range extending from the minimum wound pressure value (WPmin) of approximately 115 mmHg to the maximum wound pressure value (WPmax) of approximately 135 mm.

Figure 5:
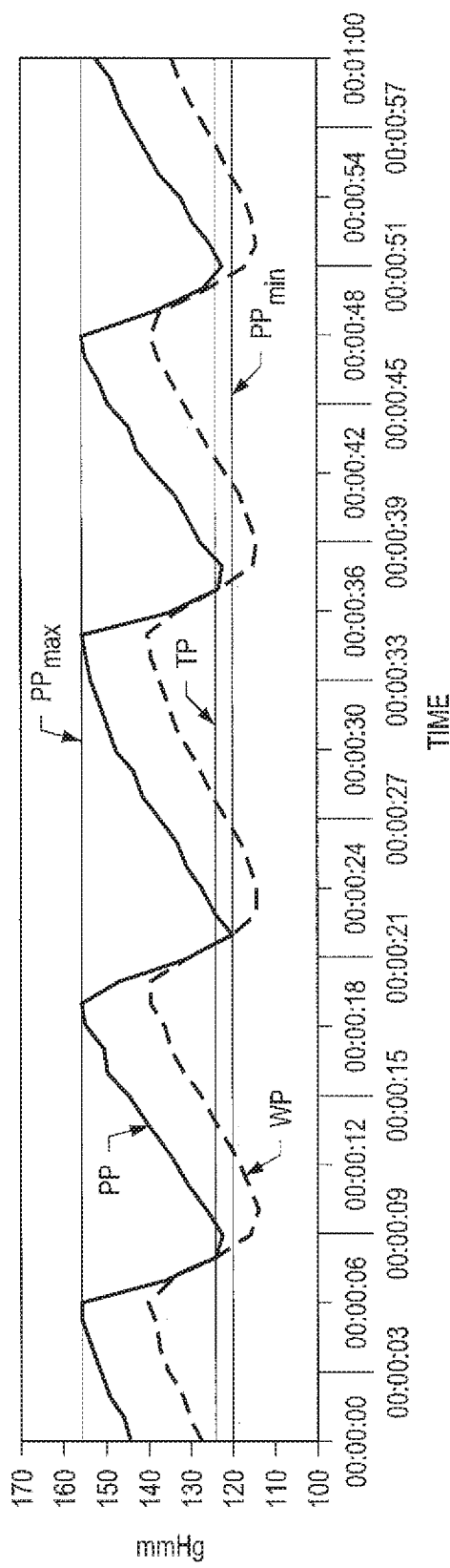
FIGS. 5 and 5A/B are graphs illustrating pressure control for a bang-bang controller in accordance with an illustrative embodiment of the example embodiment wherein the x-axis represents time in seconds (sec) and the y-axis represents pressure generated by a pump in Torr (mmHg) that varies with time in an continuous control mode and wherein the pressure control of the bang-bang controller is subjected to a larger head pressure created by the reduced-pressure's therapy system of FIG. 1 as shown in FIG. 5 compared to the smaller head pressure shown in FIGS. 5A/B, FIG. 5B having an expanded vertical pressure scale than that shown in FIG. 5A.
Figure 5A:
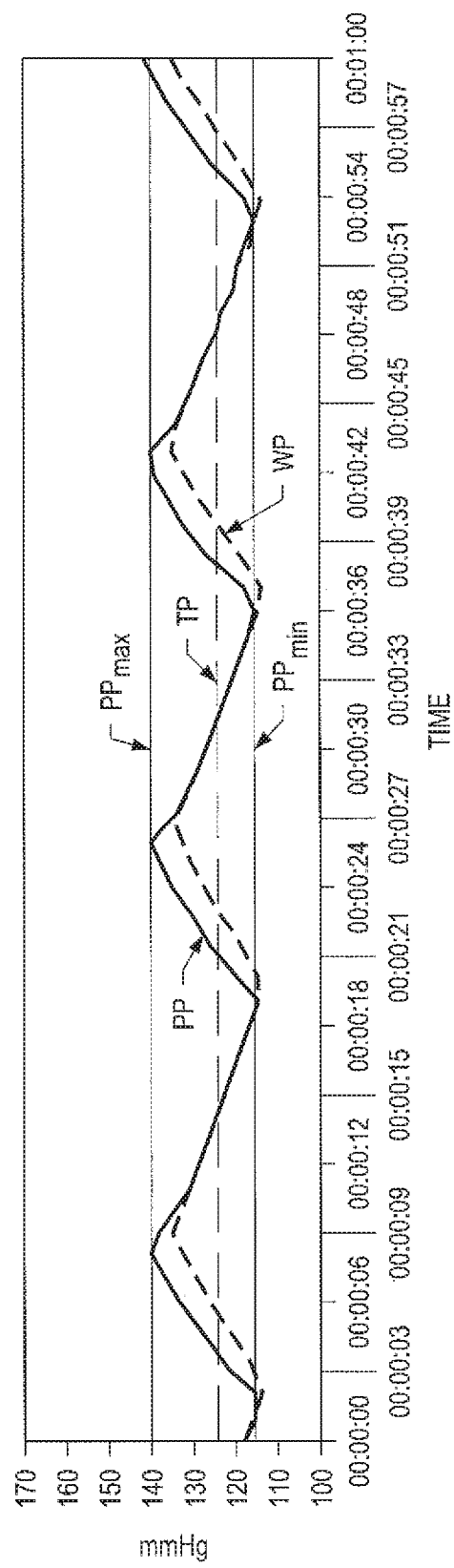
Figure 5B:
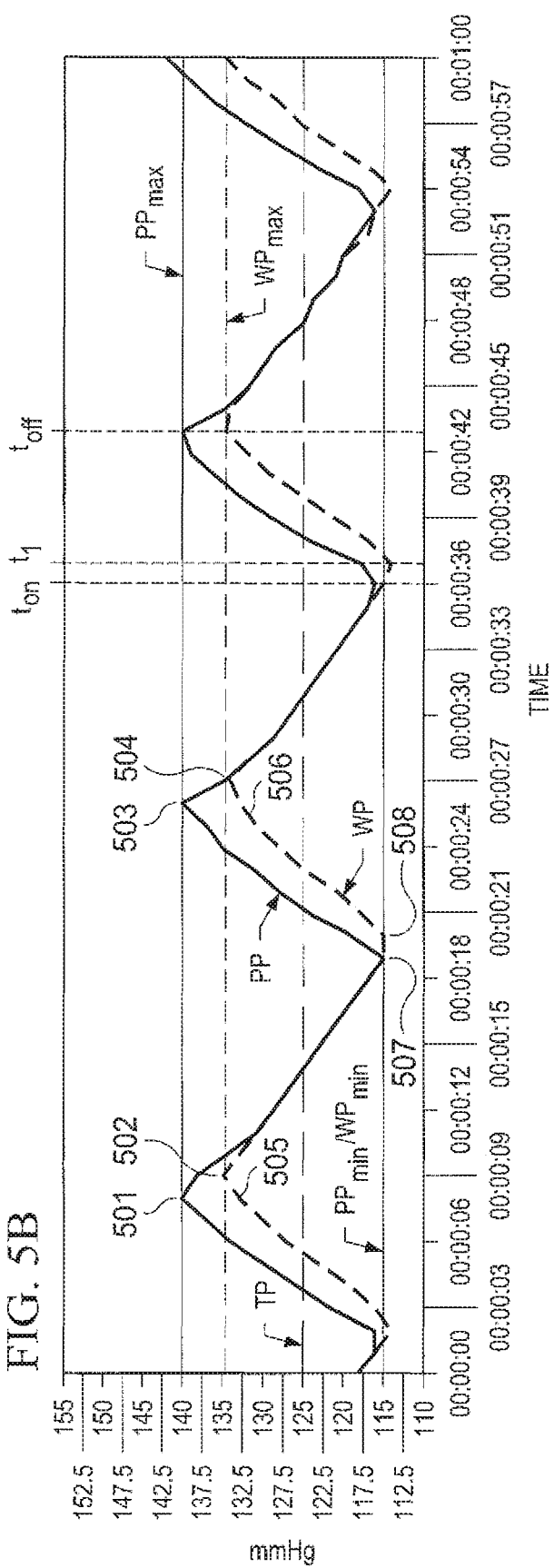

Referring to FIG. 5 as an example of wound pressure (WP) variations under normal operating conditions in contrast to the example illustrated in FIG. 4, the pressure differential ($\delta P$) between the pump pressure (PP) and the wound pressure (WP) is the result of a fairly high leakage rate (LR) of approximately 300 cc/min in the dressing 115 and other components in the system. In this example, the wound pressure (WP) is being controlled to cycle between approximately 135 mmHg and 115 mmHg as described above by providing a pump pressure (PP) that rises to a maximum pump pressure value (PPmax) of approximately 155 mmHg and drops to a minimum pump pressure value (PPmin) of approximately 120 mmHg to yield a target pressure (TP) at the tissue site 105 of approximately 125 mmHg. Thus, the pressure differential (δP) is approximately 15 mmHg which is much less than the pressure differential of approximately 50 mmHg resulting from the head pressure in the example associated with FIG. 4 above. FIGS. 5A and 5B illustrate yet another example wherein the pressure differential (δP) between the pump pressure (PP) and the wound pressure (WP) is the result of a lower leakage rate (LR) of approximately 50 cc/min in the dressing 115 and other components in the system. In this example, the wound pressure (WP) is again being controlled to cycle between approximately 135 mmHg and 115 mmHg by providing a pump pressure (PP) that rises to a maximum pump pressure value (PPmax) of 140 mmHg and drops to a minimum pump pressure value (PPmin) of 115 mmHg to yield a target pressure (TP) at the tissue site 105 of approximately 125 mmHg. Thus, the pressure differential (δP) is approximately 5 mmHg which is even less than the pressure differential in the previous example. The pressure variations shown in FIG. 5B are the same as those shown in FIG. 5A except only that the pressure variations in FIG. 5B are shown with an expanded pressure scale.

The controller 170 may also comprise a bang-bang controller (not shown) which is also referred to as an on-off controller, or a hysteresis controller. The bang-bang controller is a feedback controller that switches abruptly between two states, e.g., between on and off. Essentially, the bang-bang controller may apply an all-or-nothing form of control. A bang-bang controller may be used to generate the pressure variations described generally above in conjunction with FIGS. 5, 5A and 5B. Continuing with that general description, the bang-bang controller may operate in one mode as follows. For example, when the wound pressure (WP) drops too low to the minimum wound pressure value (WPmin), the reduced pressure pump 112 is turned on with an applied voltage ($V_A$) greater than the stall voltage, i.e., the bang-bang on voltage ($V_{ON}$) at a start time ($t_{on}$), to increase the pump pressure (PP) to the maximum pump pressure (PPmax). Although an increase in the pump pressure (PP) may slightly lag the application of the applied voltage ($V_A$), the increasing pump pressure (PP) eventually causes the wound pressure (WP) to increase as well as shown at time $t_1$. The bang-bang on voltage ($V_{ON}$) continues to be applied until the pump pressure (PP) reaches the maximum pump pressure value (PPmax) or the wound pressure (WP) reaches the maximum wound pressure value (WPmax), whichever occurs first. When either one of these maximum values is reached or exceeded, the reduced pressure pump 112 is turned off at an off time ($t_{off}$) so that no pump pressure (PP) is applied allowing the residual pressure in the reduced pressure therapy system 100 to decrease as a result of the leakage in the system. The reduced pressure pump 112 remains off until the wound pressure (WP) is again less than or equal to the minimum wound pressure value (WPmin) or the pump pressure (PP) is less than or equal to the minimum pump pressure value (PPmin), whichever occurs first. The residual pressure may also be reduced more quickly by opening a relief valve (not shown) that vents air pressure from the system.

The bang-bang controller switches between these two states wherein the reduced pressure pump 112 is turned on when the wound pressure or the pump pressure drops too low in a descending mode and turns the reduced pressure pump 112 off when the wound pressure or pump pressure rises too high in an ascending mode. Referring more specifically to FIG. 5B, the bang-bang controller allows the wound pressure (WP) to oscillate proximate the target pressure (TP) of 125 mmHg as contained between the two limits that a user programs into the controller 170, e.g., the minimum wound pressure value (WPmin) of 115 mmHg and the maximum wound pressure value (WPmax) of 135 mmHg. The wound pressure (WP) is not pulled back within the wound pressure range (δWP) of 20 mmHg unless the wound pressure (WP) exceeds either one of these limits. The bang-bang controller keeps the wound pressure (WP) substantially within this range because the bang-bang controller does not need to overcompensate for leakage in a low-leakage environment.

The controller 170 may also include a PID controller (not shown) that provides a control loop feedback mechanism that calculates an error value as the difference between a measured process variable and a desired setpoint or target, in this case the wound pressure (WP) and the corresponding target pressure (TP) at the wound site 105, respectively. PID controllers are well-known by those skilled in the art as providing proportionality information, historical information, and time rate of change information to maintain the wound pressure (WP) close to the target pressure (TP). The PID summation is used to adjust the process, in this case the reduced pressure therapy process, by a control element such as the power or voltage supplied to a DC motor, i.e. the applied voltage ($V_A$), which is directly related to the pump pressure (PP) as described above. The applied voltage ($V_A$) may be varied as described above by adjusting the pulse-width modulation to achieve the desired pump pressure (PP) necessary to compensate for the leakage of the dressing 115 and/or the pressure head referred to above. The response of the PID controller is dependent on the responsiveness of the controller to an error, the degree to which the controller overshoots the setpoint, e.g., the target pressure (TP), and the degree of system oscillation, e.g., the degree of oscillation of the wound pressure (WP) within the acceptable range described above. Although a preferred embodiment of the PID controller is a digital controller, the PID controller may also be an analog controller or a simple RC circuit. The analog or digital PID controller may be implemented in hardware components or software as part of a program logic controller well-known in the art.

After the wound pressure sensor 155 measures the wound pressure (WP), the PID controller adjusts the pump pressure (PP) by supplying the applied voltage ($V_A$) necessary for adjusting the wound pressure (WP) back to the target pressure (TP), i.e., the pump pressure correction (δPP). The pump pressure correction (δPP) is the additional pressure needed to maintain the wound pressure (WP) at the desired target pressure (TP), e.g., 125 mmHg, and may be calculated every few seconds. Consequently, the PID control varies the applied voltage ($V_A$) to the DC motor 114 to achieve a pump pressure (PP) between a minimum pump pressure value (PPmin) and a maximum pump pressure value (PPmax) which maintains the wound pressure (WP) proximate the target wound pressure (TP).

Figure 6:
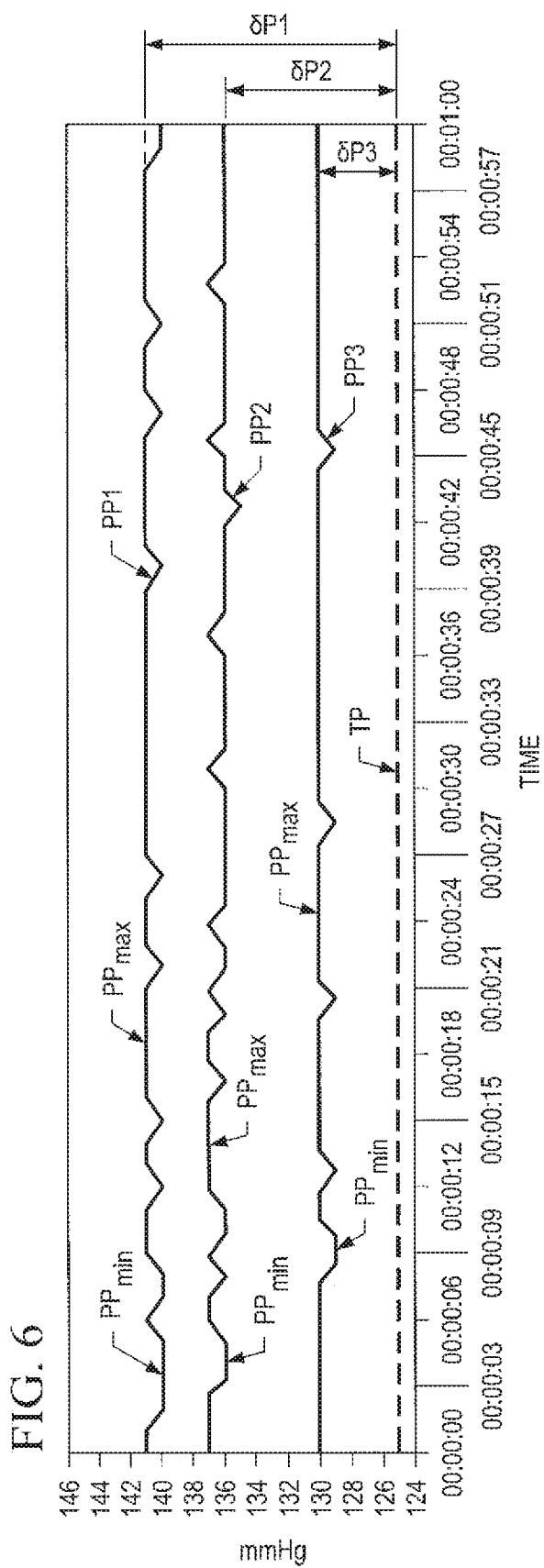
FIG. 6 is a graph illustrating pressure control for a PID controller in accordance with an illustrative embodiment of the example embodiment wherein the x-axis represents time in seconds (sec) and the y-axis represents pressure generated by a pump in Torr (mmHg) that varies with time in an continuous control mode and wherein the horizontal time scale is substantially the same as the horizontal timescale shown in FIG. 5B for comparing pressure control with that of the bang-bang controller.

Referring more specifically to FIG. 6 as an example of maintaining the wound pressure (WP) under normal operating conditions of a PID controller in contrast to the example illustrated in FIG. 4, the pressure differential (δP) between the pump pressure (PP) and the wound pressure (WP) is the result of different leakage rates (LR) as illustrated by the three examples including the first pump pressure (PP1), the second pump pressure (PP2), and the third pump pressure (PP3). In the first example, the first pump pressure (PP1) has a relatively large pressure differential (δP1) of approximately 15-16 mmHg resulting from a fairly high leakage rate (LR) of approximately 350 cc/min. The first pressure (PP1) is varied by the PID controller between a maximum pump pressure value (PPmax) and a minimum pump pressure value (PPmin) to maintain the wound pressure (WP) at the target pressure (TP) of 125 mmHg. In other words, the PID controller varies the first pump pressure (PP1) between 140 mmHg and 141 mmHg to maintain the wound pressure (WP) at the target pressure (TP) of 125 mmHg. In the second example, the second pump pressure (PP2) also has a relatively large pressure differential ($\delta$P2) of approximately 11-12 mmHg resulting from a fairly high leakage rate (LR) of approximately 250 cc/min and is varied by the PID controller between a maximum pump pressure value (PPmax) and a minimum pump pressure value (PPmin) to maintain the wound pressure (WP) at the target pressure (TP) of 125 mmHg. In other words, the PID controller varies the second pump pressure (PP2) between 136 mmHg and 137 mmHg to maintain the wound pressure (WP) at the target pressure (TP) of 125 mmHg. Fundamentally, the difference between these two examples is that the higher leakage rate (LR) requires a larger pressure differential ($\delta$P) to maintain the wound pressure (WP) at the same target pressure (TP). The third example illustrates the same difference wherein the third pump pressure (PP3) also has a much smaller pressure differential ($\delta$P3) of approximately 4-5 mmHg resulting from a lower leakage rate (LR) of approximately 100 cc/min and is varied by the PID controller between 129 mmHg and 130 mmHg to maintain the wound pressure (WP) at the target pressure (TP) of 125 mmHg.

Unlike the bang-bang controller, the PID controller does not switch the reduced pressure pump 112 on and off, but rather continuously controls the application of the pump pressure (PP) between the maximum and minimum pressure values, (PPmax) and (PPmin), to maintain the wound pressure (WP) at a relatively constant level, e.g., at a target pressure (TP) all of 125 mmHg as shown by the dashed line, rather than allowing it to vary between a maximum and minimum pressure value, (WPmax) and (WPmin) as shown with the bang-bang controller. Therefore, the extent to which the pump pressure (PP) drops towards the minimum pump pressure value (PPmin), the more that the PID controller increases the applied voltage ($V_A$) being provided to the DC motor 114. Correspondingly, the further the wound pressure (WP) varies from the target pressure (TP), the more the PID controller responds by adjusting the applied voltage ($V_A$) being provided to the DC motor 114. The action taken to increase or decrease the applied voltage ($V_A$) is proportional to the degree that the wound pressure (WP) provided by the reduced pressure system diverges from the target wound pressure (TP). The PID controller continuously operates in order to keep the wound pressure (WP) as close to the target wound pressure (TP) as possible, especially for high leakage rates (LR). Consequently, the PID controller causes the reduced pressure therapy system 100 to run smoother than the bang-bang controller as shown when comparing the wound pressure (WP) variations of FIGS. 6 and 5, respectively, because the PID controller maintains the wound pressure (WP) closer to the target wound pressure (TP) on average, while the bang-bang controller allows the wound pressure (WP) to oscillate between the two limits as described above.

When the flow rate (FR) is small enough to indicate a low leakage condition, e.g., when the pump pressure (PP) or the wound pressure (WP) is decreasing at a very slow rate toward their respective minimum pressure values, i.e., (PPmin) or (WPmin), the bang-bang controller may provide a sufficiently smooth wound pressure (WP) during treatment while conserving battery power and reducing noise by virtue of the reduced pressure pump 112 being intermittently turned off during the same treatment period. For example, the DC motor 114 and pump 112 are turned off for a significant percentage of time during the one minute period shown in FIG. 5B, but run continuously when the PID controller is operative as shown in FIG. 6. Hence, it is desirable to keep the bang-bang controller running during treatment sessions as much as possible for low leakage conditions such as, for example, when the flow rate (FR) is less than or equal to a fixed target flow rate (TFR) which represents a low leak condition, but switch to the PID controller when the flow rate (FR) is greater than the fixed target flow rate (TFR) which represents a high leak condition. Consequently, another example embodiment of the controller 170 includes both the PID controller and the bang-bang controller, i.e., a hybrid controller, and additional processing that switches between them depending on the degree of leakage of the reduced pressure therapy system 100 regardless of the location of the leaks or leakage.

Thus, the controller 170 may be programmed to use the bang-bang controller in conjunction with the PID controller operating as described above to enable or disable the PID controller depending on a specific switching condition relating to the amount of air leakage created by the dressing 115 or other components of the reduced pressure therapy system 100 that affect the flow rate (FR). Using such a hybrid controller would be preferable to utilizing only a PID controller which runs continuously during the continuous control mode as described above (or the enabled portions of an intermittent control mode as described above) to more tightly maintain the wound pressure (WP) at the target wound pressure (TP), but may continually generate noise and more rapidly drain the battery driving the motor 114. The hybrid controller may engage the bang-bang controller so that the DC motor 114 is turned on and off to conserve battery power and reduce noise generated by the pump 112 during therapy treatments. The controller 170 may further include an input for a user/caregiver to set one or more target flow rates (TFR).

The user/caregiver may set the target flow rates (TFR) as the switching condition for determining whether the dressing 115 or other components are in a high leakage state or a low leakage state. If the flow rate (FR) is greater than the fixed target flow rate (TFR), i.e., a high leak condition, the bang-bang controller is disabled so that the PID controller takes over in order to keep the wound pressure (WP) as close to the target wound pressure (TP) as possible. However, if the flow rate (FR) is less than or equal to the fixed target flow rate (TFR), i.e., a low leak condition, the bang-bang controller is enabled to contain the wound pressure (WP) within the differential wound pressure ($\delta$WP) range while conserving battery power and reducing noise from the pump 112. For example, the fixed target flow rate (TFR) may be 65 cc/min. As indicated above, it is desirable to keep the bang-bang controller running as much as possible during treatments when the dressing 115 is in a low leakage condition. For example, the controller 170 may engage the bang-bang controller when the flow rate (FR) is less than or equal to the fixed target flow rate (TFR), but switch back to the PID controller when the flow rate (FR) is greater than the fixed target flow rate (TFR) as a result of additional leakage that develops in the dressing 115 because the patient moving around which ultimately creates a high leak condition.

In another embodiment, the bang-bang controller may have a dual target flow rate (TFR) capability wherein the controller 170 further includes an input for a user to set two target flow rates (TFR) as switching conditions for determining whether the dressing 115 or other components are in a high leakage state or a low leakage state: an ascending target flow rate (TFR$_A$) when the bang-bang controller is enabled with an increasing flow rate (FR) and a descending target flow rate (TFR$_D$) when the PID controller is enabled with a decreasing flow rate (FR). In one embodiment, both the ascending target flow rate (TFR$_A$) and the descending target flow rate (TFR$_D$) are greater than the fixed target flow rate (TFR) so that the controller 170 switches more quickly from the PID controller to the bang-bang controller and more slowly from the bang-bang controller to the PID controller. For example, the ascending target flow rate (TFR$_A$) and the descending target flow rate (TFR$_D$) may both be set to about 80 cc/min which is higher than the fixed target flow rate (TFR) of 65 cc/min in the previous example. In yet another embodiment, the ascending target flow rate (TFR$_A$) may also be greater than the descending target flow rate (TFR$_D$) so that the controller 170 switches even more quickly from the PID controller to the bang-bang controller and even more slowly from the bang-bang controller to the PID controller. In this case, the controller 170 favors the benefits derived from using the bang-bang controller as opposed to the deficiencies associated with the continuous operation of the PID controller. For example, the ascending target flow rate (TFR$_A$) may be 75 cc/min and the descending target flow rate (TFR$_D$) may be about 85 cc/min. If the PID controller is currently enabled in a high leak condition wherein the flow rate (FR) is decreasing, the descending target flow rate (TFR$_D$) would be set at 85 cc/min rather than 65 cc/min so that the controller 170 switches more quickly from the PID controller to enable the bang-bang controller. Alternatively, if the bang-bang controller is enabled in a low leak condition wherein the flow rate (FR) is increasing, the ascending target flow rate (TFR$_A$) would be set at 75 cc/min rather than 65 cc/min so that the controller 170 switches more slowly to disable the bang-bang controller.

In one embodiment, controller 170 may provide an output signal to the indicator 172 to emit a visual and/or audible signal in response to the wound pressure (WP) at tissue site 105, as measured by pressure sensor 155, being nonresponsive to increasing the pump pressure (PP). For example, the indicator may be a light emitting diode (LED) that provides a visual signal. In this embodiment, indicator 172 illuminates in response to the wound pressure (WP) at tissue site 105 being nonresponsive to an increasing pump pressure. In another embodiment, indicator 180 is a sound emitting device, such as a speaker. In this embodiment, indicator 172 emits a sound in response to the wound pressure (WP) at tissue site 105 being nonresponsive to an increasing pump pressure. The controller 170 may provide other output signals indicating whether the negative pressure therapy system is in a low or high leak condition.

Figure 7:
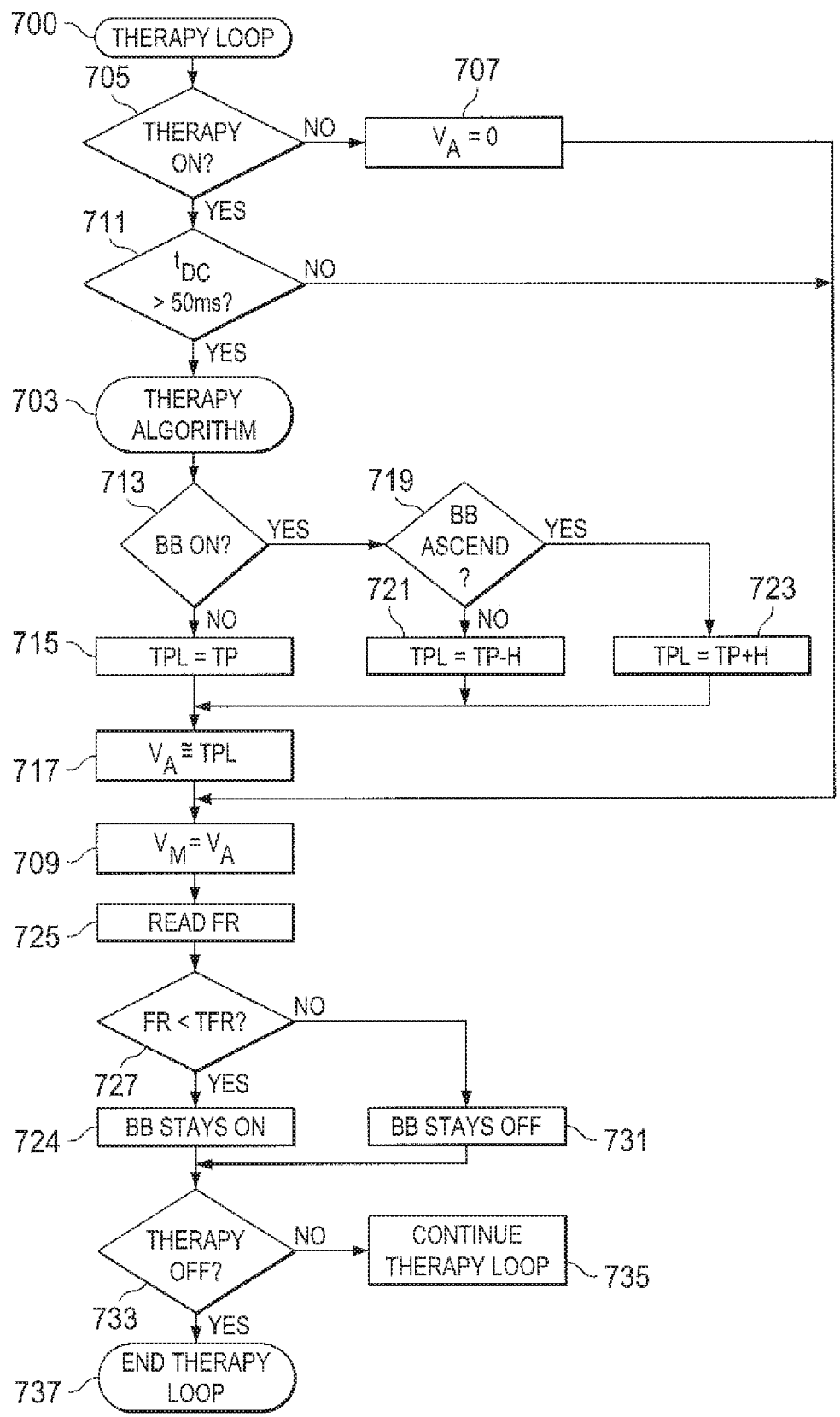
FIG. 7 is a flowchart illustrating a process or therapy loop for controlling reduced pressure at a tissue site that may be stored on the controller of FIG. 1 including a therapy algorithm for selecting the appropriate pump pressure control for controlling reduced pressure at a tissue site in accordance with an illustrative embodiment of the example embodiment.

Referring now to FIG. 7, an example embodiment of a method or process for controlling the wound pressure (WP) as implemented as a supreme controller on the controller 170 as described above or, alternatively, on another example embodiment of the controller 170 is shown. The controller 170 and other components may implement this process as described above according to a therapy loop 700 illustrated as the flowchart in FIG. 7. The therapy loop 700 includes a therapy algorithm 703 for selecting the appropriate controller, i.e., the PID controller or the bang-bang controller, for controlling the delivery of reduced pressure to the tissue site while conserving power and reducing noise from the pump 112 and the motor 114 at the same time. The controller 170 first checks to see if the negative pressure therapy system 100 has been turned on at 705 so that if the negative pressure therapy system 100 is not on, the applied voltage (V$_A$) is set to 0 V at 707 and applied to the motor 114 as a new motor voltage (V$_M$) at 709 so that the motor 114 is not running. If the negative pressure therapy system 100 is turned on, the controller 170 checks to determine whether enough time has elapsed at 711 to engage the therapy algorithm 703, i.e., the duty cycle therapy time (t$_{DC}$). The duty cycle of the therapy algorithm 703 may be, for example, about 50 ms. Thus, if less than 50 ms transpires since the therapy algorithm 703 was last calculated, the motor voltage (V$_M$) remains set at the previously applied voltage (V$_A$) at 709. The duty cycle of the therapy loop 700 itself may be, for example, 10 ms without engaging the therapy algorithm 703. However, if more than 50 ms have transpired, the controller 170 recalculates the therapy algorithm 703 and proceeds to check the current wound pressure (WP) and/or the pump pressure (PP) at 713 with respect to their corresponding maximum and minimum wound pressure and pump pressure values as described above, i.e., (WPmax) and (WPmin), and (PPmax) and (PPmin), respectively.

The therapy algorithm 703 begins by determining whether the bang-bang controller is active or not at 713. If the PID controller is engaged and the bang-bang controller is not, a local pump pressure (PPL) is set at a current pump pressure (PPC) at 715. As described above, the PID control adjusts the applied voltage (V$_A$) to the DC motor 114 to achieve a pump pressure (PP) between the minimum pump pressure value (PPmin) and the maximum pump pressure value (PPmax) to maintain the wound pressure (WP) proximate the target wound pressure (TP). Referring back to FIG. 6 as an example, the PID controller varies the first pump pressure (PP1) between 140 mmHg and 141 mmHg to maintain the wound pressure (WP) at the target pressure (TP) of 125 mmHg and continues to control the pump pressure (PP) during a high leakage condition. The controller 170 determines the value of applied voltage (V$_A$) corresponding to the current pump pressure (PPC) at 717 and applies that voltage as the motor voltage (V$_M$) at 709. However, if the bang-bang controller is engaged or active as shown in FIG. 5B, the therapy algorithm 703 determines whether the bang-bang controller is ascending or descending at 719.

When the wound pressure (WP) drops too low in the descending mode, e.g., below the minimum wound pressure value (WPmin) as described above, the reduced pressure pump 112 is turned on with an applied voltage (V$_A$) greater than the stall voltage, i.e., the bang-bang on voltage (V$_{ON}$), to increase the pump pressure (PP) to the maximum pump pressure (PPmax) in the ascending mode. The bang-bang on voltage (V$_{ON}$) continues to be applied until the pump pressure (PP) reaches the maximum pump pressure value (PPmax) as shown, for example, at 501 and 503, or the wound pressure (WP) reaches the maximum wound pressure value (WPmax) as shown, for example, at 502 and 504, whichever occurs first. When the wound pressure (WP) is in the ascending mode, the therapy algorithm 703 sets the local target wound pressure (TPL) at the target wound pressure (TP) plus a hysteresis value (H) at 723. The hysteresis value (H) is the maximum amount of pressure that the wound pressure (WP) should increase above the target wound pressure (TP) when in the ascending mode before the controller 170 turns off the pump 112 to protect the tissue site 105 from an excessive amount of reduced pressure that could be damaging. The hysteresis value (H) sets the upper limit above the target wound pressure (TP) which is the maximum pressure value (WPmax). For example, if the hysteresis value (H) is 10 mmHg, the maximum wound pressure value (WPmax) is set at 135 mmHg as shown in FIG. 5B. Because the wound pressure (WP) normally trails the ascending pump pressure (PP) as shown by the wound pressure peaks at 502 and 504, and the pump pressure peaks at 501 and 503, the wound pressure (WP) is normally less than the maximum wound pressure value (WPmax), e.g., about 132 mmHg at 505 and 506, when the pump pressure (PP) hits the maximum pump pressure value (PPmax), e.g., about 140 mmHg at 501 in 503. Consequently, the controller 170 allows the bang-bang controller to continue regulating the application of reduced pressure, but does turns off the pump 112 in the descending mode of the reduced pressure cycle.

Correspondingly, when the wound pressure (WP) rises too high in the ascending mode, e.g., above the maximum wound pressure value (WPmax) or the maximum pump pressure value (PPmax) as described above, the reduced pressure pump 112 is turned off so that no pump pressure (PP) is applied allowing the residual pressure in the reduced pressure therapy system 100 to decrease in the descending mode as a result of the leakage in the system. The reduced pressure pump 112 remains off until the wound pressure (WP) is again less than or equal to the minimum wound pressure value (WPmin) is shown, for example, at 508, or the pump pressure (PP) is less than or equal to the minimum pump pressure value (PPmin) as shown, for example, that 507, whichever occurs first. When the wound pressure (WP) is in the descending mode as described above, the therapy algorithm 703 sets the local target wound pressure (TPL) at the target wound pressure (TP) minus the hysteresis value (H) at 721. The hysteresis value (H) is the minimum amount of pressure that the wound pressure (WP) should decrease below the target wound pressure (TP) when in the descending mode before the controller 170 determines that the leakage rate (LR) has increased to a flow rate that is large enough to require the PID controller to maintain the wound pressure (WP) closer to the target wound pressure (TP) as described above. Thus, the hysteresis value (H) also sets the lower limit below the target wound pressure (TP) which is the minimum pressure value (WPmin). For example, if the hysteresis value (H) is 10 mmHg, the minimum wound pressure value (WPmin) is set at 115 mmHg as shown in FIG. 5B. Because the pump pressure (PP) normally follows the descending wound pressure (WP) as shown between the pump and wound pressure peaks at 501 and 502, respectively, and the pump and wound pressure minimums that 507 and 508, respectively, the bang-bang controller turns the pump 112 back on at 507 after which the wound pressure (WP) begins to increase again in the ascending mode. Consequently, the controller 170 allows the bang-bang controller to continue regulating the application of reduced pressure, and does so by turning on the pump 112 in the ascending mode of the reduced pressure cycle. The bang-bang controller allows the wound pressure (WP) to effectively oscillate around the target pressure (TP) of 125 mmHg as contained between the two limits that may be programmed into the controller 170 separately using the minimum wound pressure value (WPmin) of 115 mmHg and the maximum wound pressure value (WPmax) of 135 mmHg, or using the hysteresis value (H). In either case, the bang-bang controller maintains the wound pressure (WP) within a wound pressure range ($\delta$WP), e.g., a wound pressure range ($\delta$WP) of 20 mmHg.

After the therapy algorithm 703 sets the motor voltage ($V_M$) to equal the applied voltage ($V_A$) at 709 to reenter the therapy loop 700, the therapy loop 700 then reads the current flow rate (FR) measured by the controller 170 at 725 and determines whether or not the current flow rate (FR) is less than the target flow rate (TFR) at 727. If the flow rate (FR) is less than the target flow rate (TFR) indicating a low leakage condition as described above, then the bang-bang controller stays on or is enabled as indicated at 729. However, if the flow rate (FR) is greater than or equal to the target flow rate (TFR) indicating a high leakage condition as described above, then the bang-bang controller stays off or is disabled as indicated at 731. Finally, the therapy loop 700 checks to see if the negative pressure wound therapy system 100 has been turned off at 733 and, if not, continues the therapy loop as indicated at 735. If the negative pressure therapy system 100 has been turned off, the therapy loop ends at 737.

The systems, apparatuses, and methods described herein may provide significant advantages. For example, PID control algorithms constantly adjust a negative-pressure source to maintain pressure within a specified tolerance, which can be inefficient in low-leak applications, drawing more power than a simple hysteresis control algorithm. Conversely, a hysteresis algorithm can work well in low-leak applications and uses relatively little power, but can cause a negative-pressure source to turn off and on frequently in high-leak applications, which can be noisy and increase power consumption. Hybrid control, as described herein, can combine the benefits of PID and hysteresis control algorithms to minimize power consumption and noise. If a negative-pressure therapy application has a low-leak, for example, a hybrid control algorithm can select a hysteresis control algorithm to minimize power consumption. If the application changes or develops a higher leak, a hybrid control algorithm can switch to a PID control algorithm to minimize noise.

While shown in a few illustrative embodiments, a person having ordinary skill in the art will recognize that the systems, apparatuses, and methods described herein are susceptible to various changes and modifications. Moreover, descriptions of various alternatives using terms such as "or" do not require mutual exclusivity unless clearly required by the context, and the indefinite articles "a" or "an" do not limit the subject to a single instance unless clearly required by the context.

The appended claims set forth novel and inventive aspects of the subject matter described above, but the claims may also encompass additional subject matter not specifically recited in detail. For example, certain features, elements, or aspects may be omitted from the claims if not necessary to distinguish the novel and inventive features from what is already known to a person having ordinary skill in the art. Features, elements, and aspects described herein may also be combined or replaced by alternative features serving the same, equivalent, or similar purpose without departing from the scope of the invention defined by the appended claims.

What is claimed is:

1. A system for stimulating healing of tissue at a wound site, comprising:
   a dressing including a porous pad configured to be positioned at the wound site and adapted to be covered by a drape to form a seal around the wound site for maintaining a wound pressure (WP) at the wound site;
   a negative-pressure source including a pump coupled to a motor and adapted to be fluidly coupled to the porous pad for applying negative pressure to the wound site and a motor, the pump being further adapted to generate a pump pressure (PP);

a pressure sensor having an input for sensing the pump pressure (PP) and an output for providing a signal indicative of the pump pressure (PP);

a controller having an input coupled to the output of the pressure sensor and an output coupled to the motor, wherein the controller is configured to (i) determine a flow rate (FR) of fluid between the pump and the porous pad, (ii) identify a leak condition based on the flow rate (FR), and (iii) control the negative-pressure source and the wound pressure (WP) based on the leak condition; and a bang-bang controller configured to control the negative-pressure source and the wound pressure (WP) dependent on the leak condition.

2. The system of claim 1, wherein the leak condition is one of a high-leak condition and a low-leak condition.

3. The system of claim 2, wherein the controller is configured further to identify the leak condition as a low-leak condition when the flow rate (FR) is less than a target flow rate (TFR).

4. The system of claim 3, wherein the bang-bang controller is configured further to increase negative pressure at the wound site when the wound pressure (WP) is less than a minimum wound pressure ($WP_{Min}$).

5. The system of claim 4, wherein the bang-bang controller is configured to increase the negative pressure at the wound site by increasing power applied to the motor.

6. The system of claim 4, wherein the bang-bang controller is configured further to decrease negative pressure at the wound site when the wound pressure (WP) is greater than a maximum wound pressure ($WP_{Max}$).

7. The system of claim 6, wherein the bang-bang controller is configured to decrease the negative pressure at the wound site by decreasing power applied to the motor.

8. The system of claim 7, wherein the bang-bang controller is configured to increase the negative pressure at the wound site by increasing power applied to the motor.

9. The system of claim 4, wherein the target flow rate (TFR) is less than about 65 cc/minute.

10. The system of claim 4, wherein the target flow rate (TFR) is less than about 75 cc/minute.

11. The system of claim 4, wherein the target flow rate (TFR) is less than about 80 cc/minute.

12. The system of claim 1, wherein the controller is configured further to compare the pump pressure (PP) to a target pump pressure (TPP).

13. The system of claim 12, wherein the controller is configured further to vary the power applied to the motor in response to the comparison for maintaining the pump pressure (PP) proximate the target pump pressure (TPP).

14. The system of claim 1, wherein the controller is configured further to determine the flow rate (FR) based on a time rate of change of power applied to the motor.

15. The system of claim 1, wherein the controller is configured further to determine the flow rate (FR) based on a time rate of change of voltage applied to the motor.

16. The system of claim 1, wherein the controller is configured further to determine the flow rate (FR) based on a time rate of change of the current drawn by the motor.

17. The system of claim 1, further comprising a second pressure sensor having an input for sensing wound pressure (WP) and an output providing a signal to the controller indicative of the wound pressure (WP).

18. The system of claim 1, wherein the motor is a DC motor.

19. The system of claim 18, wherein power applied to the motor is varied by varying voltage applied to the DC motor.

20. The system of claim 19, wherein the voltage applied to the motor is a pulse width modulated voltage.

21. The system of claim 20, wherein the voltage is varied by varying a duty cycle of the pulse width modulated voltage.

22. The system of claim 21, wherein the controller is further configured to determine the flow rate (FR) by determining a time rate of change of the voltage applied to the motor.

23. A method for stimulating healing of tissue at a wound site, comprising:

positioning a porous pad at a wound site and covering the porous pad with a drape to form a seal for maintaining negative pressure at the wound site;

applying negative pressure to the porous pad using a pump driven by a an electric motor that generates a pump pressure (PP);

determining wound pressure (WP) proximate the wound site as a result of applying negative pressure to the porous pad;

determining a flow rate (FR) of fluids between the pump and the porous pad based on a time rate of change in power applied to the motor and identifying a leak condition based on the flow rate (FR); and selecting a method of controlling the negative-pressure source based on the leak condition determined.

24. The method of claim 23, further comprising identifying the leak condition as one of a high-leak condition and a low-leak condition.

25. The method of claim 24, further comprising identifying the leak condition as a low-leak condition when the flow rate (FR) is less than a target flow rate (TFR).

26. The method of claim 25, further comprising increasing the negative pressure at the wound site if the wound pressure (WP) is less than a minimum wound pressure ($WP_{Min}$).

27. The method of claim 25, further comprising decreasing the negative pressure at the wound site if the wound pressure (WP) is greater than a maximum wound pressure ($WP_{Min}$).

28. The method of claim 23, wherein the time rate of change in the power applied to the electric motor is determined by determining time rate of change of voltage applied to the motor.

29. The method of claim 23, wherein the time rate of change in the power applied to the motor is determined by determining time rate of change of current drawn by the electric motor.

30. The method of claim 23, further comprising comparing the pump pressure (PP) to a target pump pressure (TPP).

31. The method of claim 30, further comprising varying power applied to the motor in response to the comparison for maintaining the pump pressure (PP) proximate the target pressure (TPP).

* * * * *

UNITED STATES PATENT AND TRADEMARK OFFICE
CERTIFICATE OF CORRECTION

PATENT NO. : 11,219,711 B2
APPLICATION NO. : 16/158525
DATED : January 11, 2022
INVENTOR(S) : Loren Francis Page 1 of 1

It is certified that error appears in the above-identified patent and that said Letters Patent is hereby corrected as shown below:

In the Claims

Column 24
Line 46, In Claim 27, delete "(WP$_{Min}$)" and insert -- (WP$_{Max}$) --, therefor.

Signed and Sealed this
Ninth Day of April, 2024

Katherine Kelly Vidal
*Director of the United States Patent and Trademark Office*